United States Patent
Mistrello et al.

(10) Patent No.: US 9,809,629 B2
(45) Date of Patent: Nov. 7, 2017

(54) **HYPOALLERGENIC VARIANTS OF PHL P 5, THE MAJOR ALLERGEN FROM *PHLEUM PRATENSE***

(71) Applicant: LOFARMA S.P.A., Milan (IT)

(72) Inventors: Giovanni Mistrello, Milan (IT); Stefania Zanotta, Milan (IT); Daniela Roncarolo, Milan (IT)

(73) Assignee: LOFARMA S.P.A., Milan (IT)

(*) Notice: Subject to any disclaimer, the term of this patent is extended or adjusted under 35 U.S.C. 154(b) by 307 days.

(21) Appl. No.: 14/366,338

(22) PCT Filed: Dec. 18, 2012

(86) PCT No.: PCT/EP2012/075982
§ 371 (c)(1),
(2) Date: Jun. 18, 2014

(87) PCT Pub. No.: WO2013/092605
PCT Pub. Date: Jun. 27, 2013

(65) Prior Publication Data
US 2014/0328881 A1 Nov. 6, 2014

(30) Foreign Application Priority Data
Dec. 19, 2011 (IT) .................... MI2011A2301

(51) Int. Cl.
*C07K 14/415* (2006.01)
*A61K 39/36* (2006.01)
*A61K 36/899* (2006.01)

(52) U.S. Cl.
CPC .......... *C07K 14/415* (2013.01); *A61K 36/899* (2013.01); *A61K 39/36* (2013.01); *C07K 2319/00* (2013.01)

(58) Field of Classification Search
None
See application file for complete search history.

(56) References Cited

U.S. PATENT DOCUMENTS 7,862,828 B2 * 1/2011 Linhart ................ C07K 14/415
424/1.69
2015/0140024 A1 * 5/2015 Wald ................... C07K 14/415
424/185.1

FOREIGN PATENT DOCUMENTS

| WO | WO0222679 | 3/2002 | | |
|---|---|---|---|---|
| WO | WO0240676 | 5/2002 | | |
| WO | WO2011029869 | 3/2011 | | |
| WO | WO 2011/085783 A1 * | 7/2011 | ............. | A61K 39/36 |

OTHER PUBLICATIONS

Schramm, et al., "Allergen Engineering: Variants of the Timothy Grass Pollen Allergen Ph1 p 5b Wtih Reduced IgE Binding Capacity but Conserved T-Cell Reactivity", J. Immunol., vol. 162, No. 4: 2406-2414, 1999.
Maglio et al., "A Major IgE Epitope-Containing Grass Pollen Allergen Domain from Ph1 p 5 Folds as a Four-Helix Bundle", Protein Engineering, vol. 15, No. 8: 635-642, 2002.
Vrtala, et al., "cDNA Cloning of a Major Allergen from Timothy Grass (*Phleum prantense*) Pollen; Characterization of the Recombinant Phl pV Allergen", J. Immunol., vol. 151 No. 9: 4773-4781, 1993.
Gehlhar et al., "Investigation of Different Recombinant Isoforms of Grass Group-V Allergens (Timothy Grass Pollen) Isolated by Low-Stringency cDNA Hybridization Antibody Binding Capacity and Allergen Activity." Eur. J. Biochem, 247, 217-223, 1997.
Wald, et al., "Generation of a Low Immunoglobulin E-Binding Mutant of the Timothy Grass Pollen Major Allergen Phl p 5a", Clinical and Experimental Allergy, 37, 441-450 2007.
Wild, et al., "A Recombinant Allergen Chimer as Novel Mucosal Vaccine Candidate for Prevention of Multi Sensitivities", Allergy, 2007; 62:33-41.
Linhart, et al., "A Hybrid Molecule Resembling the Epitope Spectrum of Grass Pollen for Allergy Vaccination", J. Allergy Clin. Immunol., 2005; 115; 1010-6.
Linhart, et al., "A Hypoallergenic Hybrid Molecule with Increased Immunogenicity Consisting of Derivatives of the Major Grass Pollen Allergen, Phl p 2 and Phl p 6", Biol. Chem. 389, 925-933, 2008.
Bufe, et al., "Major Allergen Phl p Va (Timothy Grass) Bears at Least Two Different IgE-Reactive Epitopes", J. Allergy Clin. Immunol., 94, No. 2, Part 1, 173-181.
Metz-Favre, et al., "Skin Test Diagnosis of Grass Pollen Allergy With a Recombinant Hybrid Molecule", J. Allergy Clin. Immunol. 2007; 120:315-21.

* cited by examiner

*Primary Examiner* — Nora Rooney
(74) *Attorney, Agent, or Firm* — Silvia Salvadori, P.C.; Silvia Salvadori

(57) ABSTRACT

Disclosed are hypoallergenic variants of Phl p 5, the major allergen from *Phleum pratense*, and the uses thereof in the treatment of allergic diseases.

14 Claims, 9 Drawing Sheets

HYPOALLERGENIC VARIANTS OF PHL P 5, THE MAJOR ALLERGEN FROM *PHLEUM PRATENSE*

This application is a U.S. national stage of PCT/EP2012/075982 filed on Dec. 18, 2012 which claims priority to and the benefit of Italian Application No. MI2011A002301 filed on Dec. 19, 2011, the contents of which are incorporated herein by reference in their entireties.

The present invention provides hypoallergenic variants of Phl p 5, nucleic acid molecules encoding for them, pharmaceutical compositions containing the same, and their use in the immunotherapy of allergic diseases caused by pollen of *Phleum prantens*.

BACKGROUND OF THE INVENTION

Allergies are caused by an abnormality in the immune system that reacts by producing IgE antibodies to proteins which, per se, are completely harmless and mainly contained in pollens, acari, epithelia, and some foods.

Recent estimates show that more than 25% of people in industrialized nations are affected by this disease, that, persisting in time, may induce worsening of symptoms (e.g., onset of asthma), and sensitization to other allergens, thus making the choice of the most appropriate therapy more complicated (1).

Hyposensitizing specific immunotherapy (SIT), unlike pharmacological therapy, is the only form of etiological treatment of allergic diseases that is able to positively affect some immunological parameters that are the basis of the disease.

SIT consists of administration of increasing doses of standardized extracts (vaccines) obtained from the same substance causing the disease. In this way, a sort of "immunological tolerance" towards such substance is gradually induced in patients. This immunological tolerance is associated to a reduction or even disappearance of allergic symptoms.

The risk for eliciting side effects that are even severe in nature (2), also if it is considerably reduced by the use of slow-release vaccines or vaccines that are administered by alternative routes to injections, has limited SIT applicability in the therapy of allergic diseases. Moreover, as SIT is carried out by administering a mix of allergenic and non-allergenic proteins of natural origin without taking account of patient's sensitization profile, new IgE reactivities to initially harmful allergens that are present in the extract can arise.

The success of SIT is associated with a modulation of the immune response to allergenic molecules at the level of T helper cells and by the induction of blocking IgG antibodies specific for sensitising allergens. These (protective) antibodies may compete with IgE for antigen, influencing the tridimensional structure of this molecule, and inhibiting the IgE-mediated presentation of allergens to T cells, thus they interfere with cronic manifestation of atopy (3).

The development of vaccines made of recombinant proteins having less allergenicity but an unaltered immunogenic capacity might result in a further improvement in the field of allergic disease therapy.

During the last 15 years, considerable advances have been made in the field of allergen characterization thanks to the application of recombinant DNA-based technologies. cDNAs coding for main allergens are available for allergenicity studies and the development of diagnostic tests, and enable innovative SITs based on the use of purified recombinant proteins and their genetically modified variants that are characterized by reduced allergenic activity.

In the world, at least 40% of type 1 allergic patients are sensitised against pollen of grass genera belonging to the numerous family of Poaceae. About 20 species out of 9000, from five sub-families, are considered to be the most frequent cause of grass pollen allergy; the Poideae sub-family, in particular, is one of the major source of allergens in cool temperate and densely populated regions in North America, Europe and southern parts of Australia because it is largely distributed and able to produce large amounts of pollen (4).

The grass pollen allergens have been classified in different groups according to their cross-reactivity. Up to 13 families of allergens have been described within Pooideae, out of which group 1 and 5 allergens appear to be the most clinically relevant, since 95 and up to 85% of patients with grass allergy, respectively, are sensitized to them. IgE antibodies against these two classes of major allergens represent 80% or more of specific IgE in patients' sera.

Group 1 allergens are glycoproteins with a molecular weight around 30-35 kDa, with similar biochemical and functional properties to β-expansins, enzymes belonging to the family of cystein-proteinases involved in the processes of growing, differentiation, fertilization and ripening of the fruits. Sequencing of the group 1 allergens from eight species has revealed a 90% level of amino acid conservation.

Group 5 allergens are non-glycosylated proteins with a molecular weight around 28-32 kDa which share a high degree of amino acid sequence identity (55-80%) which confers them cross-reactivity in both IgE binding and T-cell reactive epitope; one of their members (Phl p Vb) was reported to have ribonuclease activity.

Within Pooideae sub-family, *Phleum pratense* pollen is the most studied, because it represents an important cause of rhinitis, conjunctivitis and bronchial asthma (5); this pollen has been often utilized as source for allergen isolation and cloning, and can be considered representative of the whole sub-family and suitable for allergen-specific immunotherapy against allergy to Poideae grass pollens (6).

The two main allergens in *Phleum pratense* pollen are Phl p 1 (whose nucleotide sequence is identified by GenBank Acc. No. X78813) and Phl p 5 (7).

Phl p 5 is represented by several isoforms which can be discerned in two main groups denoted a (AF069470) (8) and b (Z27083). Incubation of natural Phl p 5, separated by 2D electrophoresis, with specific IgE antibodies revealed that each one of the two isoforms is divided in at least four isoallergens bearing identical epitopes but at least one different epitope, located on both the C-terminal and N-terminal of the molecule.

In recent years, most attention has been focused on the development of safer, more effective vaccines, consisting of recombinant proteins mutagenised at the level of amino acids important for IgE binding, namely hypoallergenic variants capable of favourably influencing the natural progression of the disease without causing undesired side effects (9).

Numerous studies have been performed to identify or alter IgE epitopes of major allergen Phl p 5 from *Phleum pratense* or of omologous proteins produced in other grasses belonging to the Pooideae sub-family.

Concerning Phl p 5b isoform, conformational nature of some IgE epitopes was shown. Using site-directed mutagenesis, 10 surface-exposed lysines out of the 12 lysines located in the C-terminal half of the molecule were substituted by alanines. IgE binding capacity of lysine-deficient mutant was significantly diminished as demonstrated by ELISA inhibition tests and basophil stimulation, and in vivo skin prick tests (SPT). The ability to induce specific IgG antibodies was unchanged demonstrating that substitution of those lysine amino acids did not hamper structural protein integrity (10).

The construction of point and deletion Phl p 5b mutants showed that IgE-binding capacity of the molecule was reduced in dependence of the length of the deletion. Mutants lacking parts of the molecule, like the stretches of aminoacids 49-133 (DM1), 50-178 (DM2), 153-178 (DM3), 71-91 coupled with 153-178 (DM4), or carrying the following point mutations A13C, N32D, N38D, D49L, K50A, A156T, A220T, A241T were analysed. Introduction of these point mutations or the shorter deletion DM3 did not affect IgE-binding capacity of these variants, in contrast the larger deletions in DM2 and DM4 mutants caused a strong reduction of IgE reactivity in vitro (by ELISA inhibition and histamine release assay) and in vivo (SPT). Mutants lacking individual epitopes were not able to induce proliferation of T cells specific for these epitopes. The best compromise was found in the case of mutant DM4, where autors observed a nearly complete reduction of IgE-binding capacity together with an overall conserved cells reactivity (11).

Based on the successful results obtained by Schramm (11) and the high sequence homology displayed by the two isoforms, the effect of some deletions studied in Phl p 5b was tested on corresponding regions in Phl p 5a molecule. It was observed that double-deletion mutant Phl p 5a Δ(94-113, 175-198) showed strongly diminished IgE-binding in immunoblot assay and IgE-inhibition tests, and an 11.5-fold reduced capability to activate basophils compared with the recombinant wild-type molecule. T cell proliferation assays demonstrated retention of stimulating capacity of double-deletion mutant. The mutant characterised by single deletion Δ94-113, corresponding to elix 3 and located in the N-terminal of the molecule, showed a reduced IgE-binding only in a subgroup of allergic patients'sera and a reduced capacity to induce histamine release by basophils. Deletion Δ175-198 alone located in the C-terminal caused a higher reduction in IgE-binding than Δ94-113 deletion, but lower than double-deletion (12).

To confirm the presence of important epitopes in the N-terminal region of Phl p 5a, the fragment Phl p 5a (56-165), comprising about one-third of the full-length molecule, was characterised. This study demonstrated this fragment represents an immunodominant portion of the allergen and contains IgE epitopes, as it strongly reacts with serum IgE from 90% of tested grass pollen allergic patients (13).

Based on B- and T-cell epitope mapping studies and on sequence comparison of group 5 allergens from different grasses, the sequence of Lol p 5, the group 5 allergen from ryegrass, was modified by site-directed mutagenesis in five highly conserved domains (D1-D5). Replacement of the aminoacids K57A (D1), K172N, F173L, T174A, V175A (D2), A204G, V205A, K206A (D3), G273A (D4), K275A (D5), combined in different ways to obtain multiple-mutants, led to a reduction of IgE binding capacity and allergenic activity, as determined by basophil histamine release and SPT in allergic patients, but did not affect the ability to induce T cell proliferation. This work demonstrated that an immunodominant B-cell epitope in Lol p 5 involves D2 domain (14).

The possibility to use engineered multimeric molecules consisting of different allergens from the same organism or different organisms for specific hyposensitising therapy has long been considered fascinating. This approach allows a number of allergens to be assembled in a single molecule with the advantage of producing a single preparation containing the allergens in a precise molar ratio.

It has been demonstrated that immunogenity of two hypoallergenic molecules can be increase by assembling them as a single hybrid molecule. Concerning grass allergy, the association of Phl p 1 and Phl p 5 in a single hybrid molecule should represent the T-epitope repertoire of both molecules, and may induce a strong IgG protective response against both allergens.

Linhart et al. (15) developed an engineered hypoallergenic molecule composed of Phl p 2 and Phl p 6 allergens, where Phl p 2 nucleotide sequence was disrupted by fragmentation, reassembled in altered order and fused with a truncated Phl p 6 sequence. The hybrid retained the reduction of IgE reactivity and allergenic activity of its components as shown by ELISA and basophil activation assays. Immunization of mice with the hybrid molecule demonstrated the increased immunogenicity of this hybrid molecule, leading to higher levels of allergen-specific IgG antibodies compared to the single components.

An engineered molecule was developed by assembling of cDNAs coding for the four major *Phleum pratense* allergens Phl p 1, Phl p 2, Phl p 5, Phl p 6. The hybrid contained most of the B-cell epitopes of grass pollen and could be used to diagnose allergy in 98% (n=652) of patients allergic to these plants. Immunization of mice and rabbits with the hybrid molecule induced stronger and earlier IgG antibody response than equimolar mixtures of the single components (16). Results from a later work confirmed the capacity of this hybrid, consisting of four major allergens, of replacing traditional *Phleum pratense* pollen extract for the in vivo diagnosis of grass pollen allergy by means of SPT (17).

As conventional immunotherapy is more effective in patients with allergic mono-sensitivities compared with multi-sensitised subjects, an allergen chimera was genetically engineered for treatment of multi-sensitisation to birch and grass pollen. The major birch pollen allergen Bet v 1 served as a scaffold for N- and C- terminal linkage of the immunodominant peptides of the major *Phleum pratense* pollen allergens Phl p 1 and Phl p 5. The chimera was immunogenic in mice for T and B cell responses to the three allergens. Intranasal application of the chimera prior to poly-sensitization significantly suppressed humoral and cellular Th2 responses specific for the three allergens and prevented development of airways inflammation upon allergen challenge with *Phleum pratense* and birch pollen extracts (18).

The data available in the literature show the regions where IgE epitopes of the grass pollen allergens, in particular belonging to the group 5, are located, without indicating the single aminoacids involved in IgE binding.

On the basis of current knowledge, most of the grass allergic patients is mainly sensitized against Group 1 and 5 allergens. The use of a highly purified hypoallergenic hybrid variant like Phl p 1-Phl p 5 might induce a targeted response to the two main allergens and eliminate the traditional therapy-related side effects caused by strong allergenic activity of crude extract and presence of numerous further molecules.

Contrary to the results proposed by Wild (18) where chimeric allergen exclusively included the immunodominant epitopes of Phl p 1 and Phl p 5, the association of the two complete allergens would represent the whole repertoire of T epitopes, and might induce a strong protective IgG response in a wider allergic population.

DISCLOSURE OF THE INVENTION

It has now been found that binding of Phl p 5 allergen to IgE can be reduced by modifying its sequence through substitution of specific amino-acid residues.

According to a first aspect thereof, the invention provides a sequence variant of Phl p 5 derived from the major allergen of *Phleum pratense* Phl p 5 (wt sequence SEQ ID NO:1), or from an isoform thereof having at least 94% sequence identity with SEQ ID NO:1, preferably at least 96%, the said variant being characterised by:

a) reduced reactivity to IgE compared to wild-type Phl p 5 SEQ ID NO:1;

b) an amino-acid sequence which presents a substitution in the Pro residue in position 158 of SEQ ID NO: 1, or, when the variant derives from a Phl p 5 isoform, it presents a substitution in the corresponding position of said isoform, i.e. in the position matching residue 158 of SEQ ID NO:1 in an alignment of Phl p 5 isoform sequence with SEQ ID NO:1.

The isoforms of Phl p 5 having at least 94% sequence identity with SEQ ID NO:1 include the natural sequences deposited at accession numbers Phl p 5.0101 (Uniprot Q40960) 97%, Phl p 5.0102 (Uniprot Q40962) 96%, Phl p 5.0104 (Uniprot P93467) 94%.

The preferred variants of allergen Phl p 5 are those wherein residue Pro 158 is substituted with a neutral, polar, acid or basic amino acid, which is preferably selected from Leu, Ala, Thr, Gly, Ile, Ser, Phe, Lys, Arg, Glu, Asp, and more preferably from Ala, Thr, Ser, Gly, Lys, Arg, Glu, Asp.

In a preferred embodiment, the variant according to the invention bearing one substitution has the sequence identified in SEQ ID NO: 2.

The substitution variant of allergen Phl p 5 according to the present invention shows an IgE reactivity reduction by at least 10% compared with the wild-type molecule, preferably by at least 30%, and more preferably by at least 60%, to the serum of patients allergic to *Phleum pratense*.

The IgE reactivity of variant SEQ ID NO: 2 was analysed in a pool of sera from allergic individuals by ELISA assay (FIG. 1). When incubated with a pool of sera from eleven patients allergic to *Phleum pratense* pollen, said variant presented a mean reduction in IgE reactivity compared with wt allergen Phl p 5 (SEQ ID NO: 1) of 61% (SEQ ID NO: 2).

These results were confirmed by ELISA-inhibition experiments, which allow to evaluate the reactivity of homologous epitopes from different proteins. It was found that with 3.125 pmol/ml of inhibitor, binding of the wt Phl p 5 protein (SEQ ID NO: 1) to IgEs from a pool of sera is inhibited by 73.2% when the serum is pre-treated with the same protein, and by 20.4% when pre-incubated with variant SEQ ID NO: 2 (FIG. 2).

These results clearly indicate that substitution of the amino acid in position 158 of SEQ ID NO: 1 interferes with the recognition of Phl p 5 allergen by IgEs.

Wt Phl p 5 allergen SEQ ID NO: 1 and the hypoallergenic variant SEQ ID NO: 2, used to immunise Balb/c mice, induce a specific IgG response (FIG. 3). In particular, the antibodies produced against SEQ ID NO: 2 also recognise the wt counterpart SEQ ID NO: 1 (FIG. 4), demonstrating that modification of the residue in position 158 does not cause a significant alteration in the IgG epitopes of the molecule. Moreover, immunisation with variants SEQ ID NO: 1 and SEQ ID NO: 2 induces a faster immune response to *Phleum pratense* pollen extract (Phl p) than that obtained with the same extract (FIG. 5). Conversely, the antibodies present in the serum of animals immunised with an unrelated antigen are unable to recognise wt Phl p 5 and *Phleum pratense* pollen extract. Reactivity to *Phleum pratense* pollen extract of the antibodies induced by immunising mice with SEQ ID NO: 1 and 2 reaches the maximum in the second week, when very weak recognition by the antibodies produced by immunising with *Phleum pratense* pollen extract is observed (FIG. 5).

Concerning the induction of protective antibodies able to compete in binding between Phl p 5 and IgE, it has been observed that the IgG antibodies produced against SEQ ID NO: 2 inhibit the binding of Phl p 5 to IgEs of patients allergic to grass with the same efficacy than IgGs induced by wt protein (SEQ ID NO: 1) (FIG. 6). ELISA inhibition experiments have demonstrated that the IgGs from mice immunised with SEQ ID NO: 2 inhibits the IgE reactivity of seven patients sera to Phl p 5 by an average of 69.1% (with values ranging from 48.3 to 82.4%), and those produced against SEQ ID NO: 1 by 71.7% (49.5-84.3%). The serum of the not-immunised animals used as control does not give rise to any inhibition of specific IgE-Phl p 5 binding.

A further aspect of the present invention relates to an immunologically active peptide corresponding to a Phl p 5 fragment containing the substitution described above. Said peptide preferably contains 15 to 35, and more preferably 15 to 20, amino-acid residues. As used herein, the expression "immunologically active" means that the peptide must be able to stimulate an IgE-independent immune response.

Another aspect of the invention relates to a hybrid protein containing a sequence variant of the major allergen of *Phleum pratense* Phl p 5 as described herein and a hypoallergenic variant of the Phl p 1 major allergen of *Phleum pratense* pollen, possibly separated by a linker.

In the hybrid protein according to the invention, said hypoallergenic variants of Phl p 5 and Phl p 1 are indifferently positioned at the amino or carboxy-terminus with head-to-tail orientation; in other words, when the amino-terminus of the hybrid protein coincides with the amino-terminus of Phl p 1 or Phl p 5, the carboxy-terminus of the hybrid protein coincides with the carboxy-terminus of protein Phl p 5 or Phl p 1 respectively. According to a preferred embodiment, the amino-terminus of the hybrid protein is occupied by Phl p 1, and the carboxy-terminus by Phl p 5 (FIG. 7).

The linker that separates the mutated sequences of Phl p 1 and Phl p 5 preferably consists of a chain of 8 amino acids, more preferably a chain of two amino acids, and even more preferably of dipeptide EF (Glu-Phe).

In a preferred embodiment of the invention, the hybrid protein contains the hypoallergenic variant of Phl p 1 described in International patent application WO2002/022679 filed by Consiglio Nazionale delle Ricerche, and entirely incorporated here by reference. In particular, the hypoallergenic variant of Phl p 1 contained in the hybrid protein according to the invention is obtained from a protein of sequence SEQ ID NO:5 or an isoform thereof which is at least 85%, and preferably at least 90% identical to said sequence SEQ ID NO:5, by substituting the Lys residues in position 28, 35, 44, 48, 179, 181, 183 and/or 185 (in the case of SEQ ID NO:5), or in the corresponding positions of said isoform, with neutral or polar amino acids preferably selected from Ala, Thr, Gly, Pro, Leu, Ile, Phe e Ser, and more preferably Ala. In a preferred embodiment, said hypoallergenic variant of Phl p 1 is SEQ ID NO:6. The hypoallergenic variants of Phl p 1 referred to here are described in the patent application cited above.

The isoforms of Phl p 1 having over 85% sequence identity with SEQ ID NO:5 include the natural molecules deposited under accession numbers Phl p 1.0101 (Uniprot Q40967) 93%, Phl p 1.0102 (Uniprot P43213) 99%.

The hybrid protein of sequence SEQ ID NO:4 wherein the hypoallergenic variant of Phl p 1 (SEQ ID NO: 6) binds to the hypoallergenic variant of Phl p 5 (SEQ ID NO:2) with head-to-tail orientation (Phl p 1→Phl p 5) via dipeptide linker EF, is particularly preferred.

The hybrid variant according to the present invention shows an IgE-binding reduction by at least 10%, preferably at least 25% compared to the wt hybrid.

The IgE reactivity of variant SEQ ID NO: 4 was analysed in a sera pool from individuals allergic to *Phleum pratense* pollen by ELISA assay (FIG. 8). When incubated with the sera, said variant (at 3.125 nM) exhibited a mean reduction of 27% in IgE reactivity compared with the wt hybrid (SEQ ID NO: 3).

These results were confirmed by ELISA-inhibition experiments. It has been observed that at equal concentrations (150 nm/ml) of inhibitor, binding between *Phleum pratense* pollen extract adsorbed on wells and the specific IgEs contained in the sera of 10 patients is inhibited, on average, by 71.7% when the serum is pre-treated with *Phleum pratense* pollen extract, by 51% when pre-incubated with a mixture of the single wt allergens, by 35.1% when pre-incubated with a mixture of the two mutagenised components, by 54.3% when pre-treated with SEQ ID NO: 3, and by 44.5% when the serum is pre-incubated with SEQ ID NO: 4 (Table 2 and FIG. 9). The ability of mutant hybrid SEQ ID NO: 4 to compete in *Phleum pratense*-IgE binding diminishes significantly compared with both SEQ ID NO: 3 (p<0.0001) and the *Phleum pratense* pollen extract.

At the same quantity (6.25 pmol/ml) of inhibitor, binding between a mixture of the single wt allergens (SEQ ID NO: 1 and SEQ ID NO: 5) adsorbed on wells and the specific IgEs contained in a pool of patients'sera is inhibited by an average of 91.4% when the serum is pre-treated with the wt hybrid (SEQ ID NO: 3), and 43.4% when pre-incubated with the mutagenised hybrid SEQ ID NO: 4 (FIG. 10).

It was also observed that the hypoallergenic variant SEQ ID NO:4, used to immunise Balb/c mice, induces the production of specific IgGs able to recognise components present in *Phleum pratense* pollen extract (FIG. 11). The hybrid molecule SEQ ID NO:4 induces a specific IgG response similar to that induced in mice by SEQ ID NO: 3, or by a mixture of the respective wt or mutagenised allergens. Moreover, immunisation with *Phleum pratense* pollen extract induces a smaller production of specific IgGs because, after two weeks of treatment, IgG response is 4.5-fold reduced compared with the response obtained with SEQ ID NO: 4.

The analysis of IgG reactivity induced by immunising mice with *Phleum pratense* pollen extract shows that IgG response to the two major allergens is very late: the response towards Phl p 5 (SEQ ID NO: 1) is observed from the second week of treatment (FIG. 12) whereas, towards Phl p 1 (SEQ ID NO: 5), it is later and detectable by ELISA assay in the seventh week after the first immunisation (FIG. 13). Conversely, SEQ ID NO: 4 strongly induces the production of IgGs able to recognise the two major allergens Phl p 1 and Phl p 5. To support the specificity of the response described above, the antibodies present in the serum of animals immunised with an unrelated antigen are unable to recognise *Phleum pratense* pollen extract, SEQ ID NO: 3 and 4 and the mixtures of wt and mutagenised variants.

Concerning the induction of protective antibodies able to compete in binding between allergen and IgE, it has been observed that the IgG antibodies produced against SEQ ID NO: 4 inhibit the binding of *Phleum pratense* pollen extract to IgEs of patients allergic to *Phleum pratense* more effectively than the mixture of the two mutagenised variants (mix mut) (p<0.001) (FIG. 14). ELISA inhibition experiments have demonstrated that the IgGs from mice immunised with SEQ ID NO: 4 inhibit the IgE reactivity of seven patients' sera by an average of 51.9% (with values ranging from 36.3 to 70.8%), and those produced against the mixture of the two mutagenised variants (mix mut) by 35.8% (14.6-52.3%); IgGs antibodies induced against the mixture of wt proteins (mix wt) inhibit the binding by an average of 52.2% (42.2-67.6%), those produced against the wt hybrid SEQ ID NO: 3 by 28.4% (1.2-49.1%), and those induced by immunisation with *Phleum pratense* pollen extract by 45.9% (11.3-64.8%). The serum of the not-immunised animals used as control does not give rise to any inhibition of specific IgE-*Phleum pratense* pollen binding.

The substitution variants according to the invention can easily be prepared by mutagenesis of the cDNA sequence of Phl p 5 (SEQ ID NO: 7), Phl p 1 (SEQ ID NO: 11), their isoforms or natural variants, or of the cDNA sequence of the wt hybrid (SEQ ID NO: 9), using techniques known to the skilled person (19).

SEQ ID NOs: 8 and 10 report the cDNA sequences encoding for the (monomeric) single-substitution variant or the hybrid variant identified as SEQ ID NOs: 2 and 4 respectively.

Further aspects of the invention therefore relate to a nucleic acid molecule encoding for a variant of allergen Phl p 5 described herein, for a peptide deriving from it or for the hybrid protein Phl p 1-Phl p 5, and an expression vector containing said molecule together with elements for expression control in eukaryotic or prokaryotic cells, such as transcription promoters or enhancers, signal sequences or other transcription regulation sequences. The vector can be a plasmid, virus, phage or any other vector commonly used in genetic engineering.

The invention also includes a prokaryotic or eukaryotic host cell transformed or transfected with the vector according to the invention. Prokaryotic cells such as *Escherichia coli* and *Bacillus subtilis*, or eukaryotic cells such as *Saccharomyces cerevisiae*, are generally used for vector cloning and cDNA expression.

The hypoallergenic variants according to the invention can also be produced as fusion proteins.

In view of their reduced IgE reactivity, the Phl p 5 variants according to the present invention could conveniently be employed to prepare pharmaceutical compositions (e.g. tablets) for use in immunotherapy of patients allergic to *Phleum pratense* pollen.

A further aspect of the invention therefore relates to a pharmaceutical composition containing an effective quantity of hypoallergenic variant of Phl p 5, or of the hybrid protein Phl p 1/Phl p 5, optionally in combination with other *Phleum pratense* allergens, together with pharmaceutically acceptable carriers, excipients or adjuvants. In a preferred embodiment, said pharmaceutical composition is in the form of a suitable vaccine for preventive or therapeutic treatment of allergic diseases, such as bronchial asthma, rhinitis, allergic conjunctivitis and allergic oral syndrome (5, 21). The sublingual, intranasal, subcutaneous and transdermal administration forms are most preferred.

The vaccination principles and methods are known to the skilled person and described, for example, in (20).

The examples below illustrate the invention in greater detail.

EXAMPLES

Unless otherwise indicated, the methods used in the following examples are described in Sambrook, Fritsch E T Maniatis "Molecular Cloning: A Laboratory Manual" II Ed. Vol. 1-2-3 CSH Lab Press 1989.

Example 1

Site-Specific Mutagenesis of the cDNA Coding for Phl p 5 Allergen

Site-specific mutagenesis of the cDNA coding for wt Phl p 5 allergen (SEQ ID NO: 7, preceded at 5' by a sequence coding six histidines) was carried out by cDNA cloning in a prokaryotic vector (pBluescript, GenBank acc. n. X52327) followed by PCR amplification. The oligonucleotides used as primers in the PCR reaction (Table 1) carried the appropriate base substitutions. For each mutagenesis, a complementary oligonucleotide binding to a corresponding region of the DNA strand was used (19). After amplification, the unaltered original template was selectively degraded with enzymatic digestion catalyzed by the restriction enzyme Dpn I. *Escherichia coli* cells were then transformed with the mutagenized molecules. Clones obtained from single bacterial colonies were sequenced according to Sanger to determine the correct base modification and the absence of non-specific mutations in the cDNA.

TABLE 1

Sequences of the oligonucleotides used as primers in site-specific mutagenesis. The mutated bases are in bold character.

| Oligonucleotide | Sequence |
| --- | --- |
| Phl p5 P158L | Caa ggt tat cct tgc cgg cga gct g (SEQ ID NO: 13) |

Example 2

Construction of a Plasmid Coding for Wild-Type Phl p 1-Phl p 5 Hybrid Molecule (wtHybrid)

The hybrid molecule containing the genetic information for wild-type Phl p 1-Phl p 5 hybrid was obtained by fusion of cDNAs coding for the single allergens.

The cDNAs encoding mature Phl p 1 and Phl p 5 proteins were obtained separately by PCR using Php1 DIM Kpn FW (Cgc ggtacc atc ccc aag gtt ccc ccg gg—SEQ ID NO: 14) and Php1 DIM Eco RV (Gc gaattc ctt gga cga gta gct ggt—SEQ ID NO: 15) oligonucleotide primers for Phl p 1 and Php5 DIM Eco FW (cgc gaattc gcc gat cta ggt tac ggc cc—SEQ ID NO: 16) and Php5 DIM Bam RV (Gcg ggatcc tca gac ttt gta gcc acc—SEQ ID NO: 17) oligonucleotide primers for Phl p 5. Phl p 1 SEQ ID NO: 11 and Phl p 5 SEQ ID NO: 7 cDNAs were used as templates.

Figure 8:
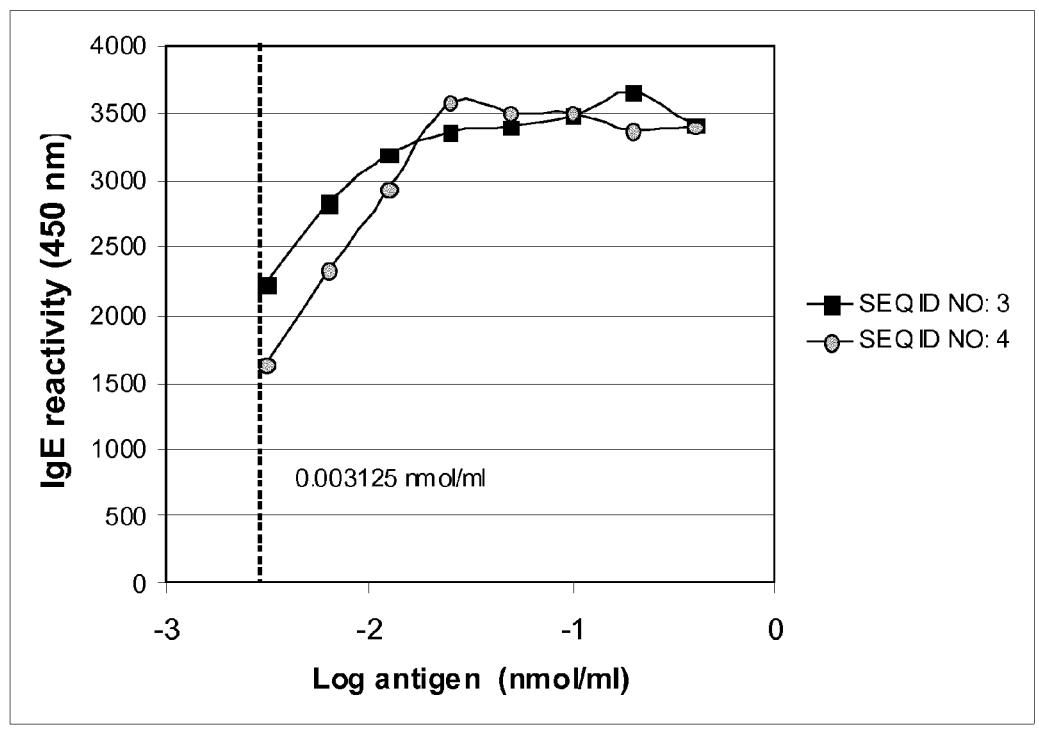
FIG. 8: ELISA analysis of IgE reactivity to hybrid variant SEQ ID NO: 4
Figure 9:
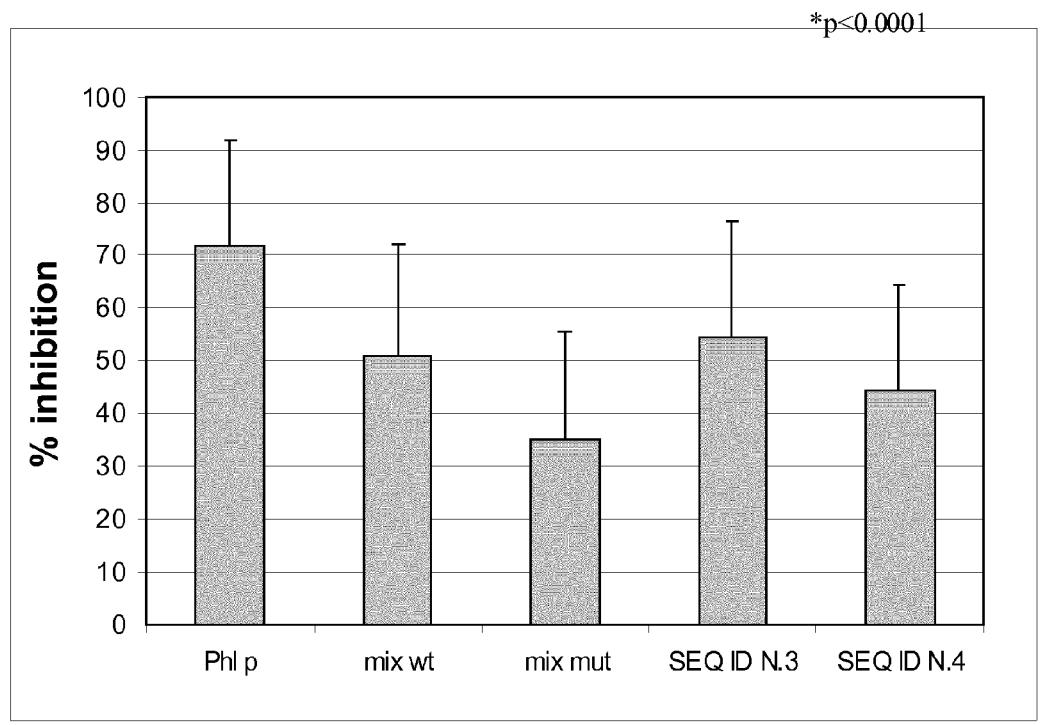
FIG. 9: Inhibition of IgE binding to Phl p pollen extract
Figure 10:
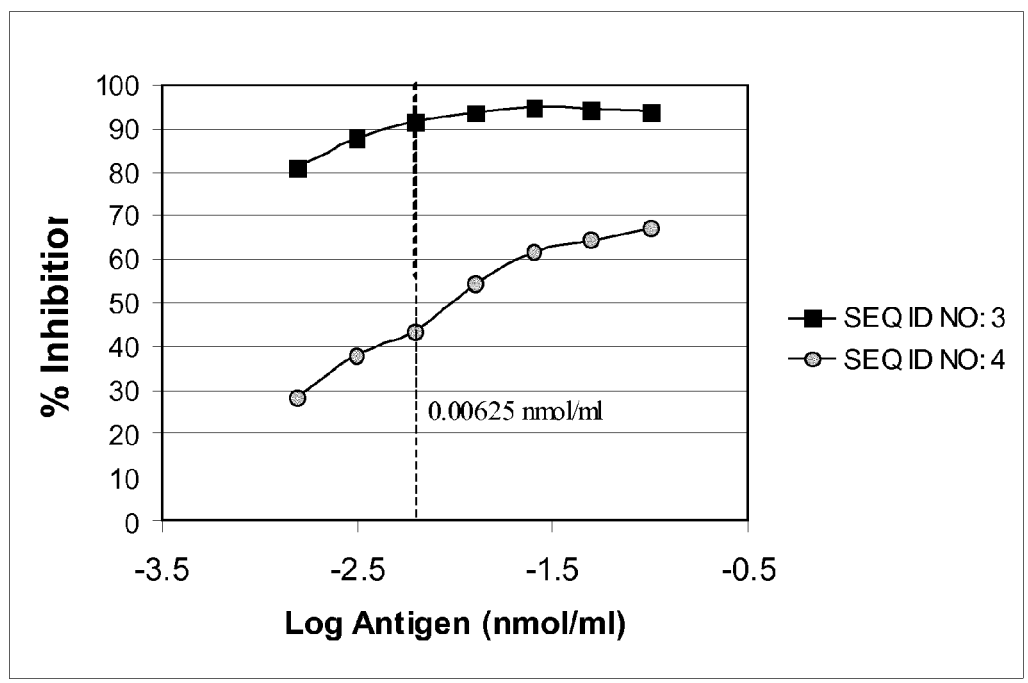
FIG. 10: Inhibition of IgE binding to (mix wt)
Figure 11:
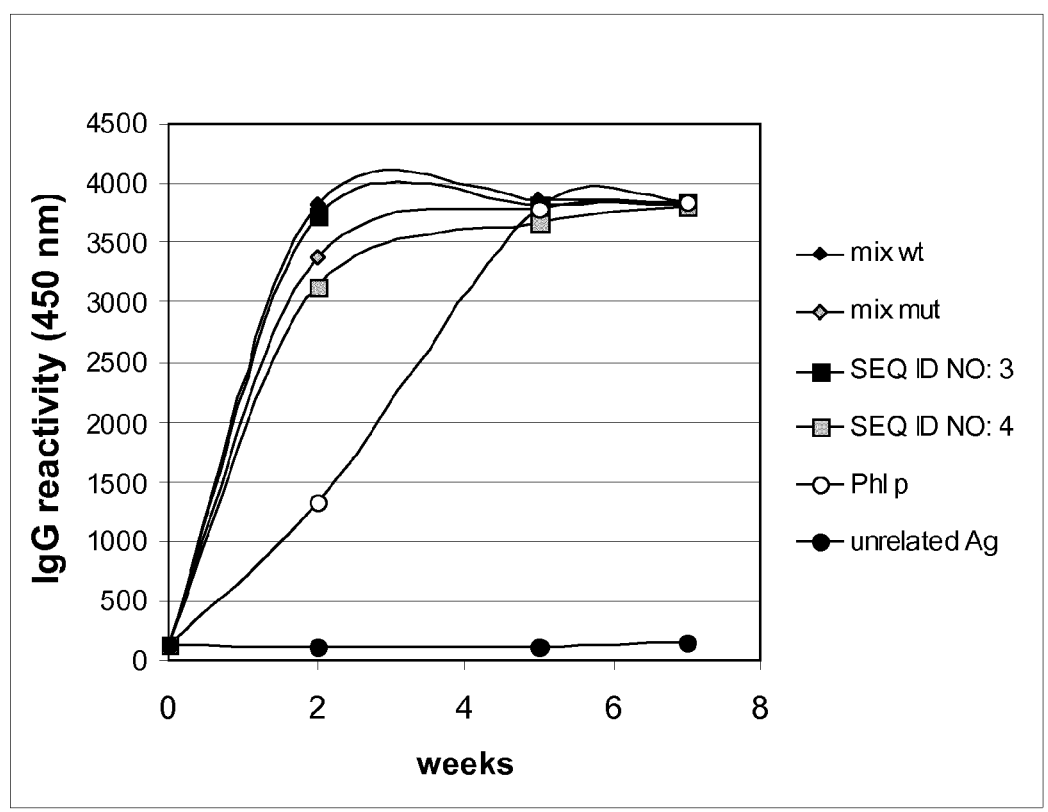
FIG. 11: Murine IgG response to Phl p
Figure 12:
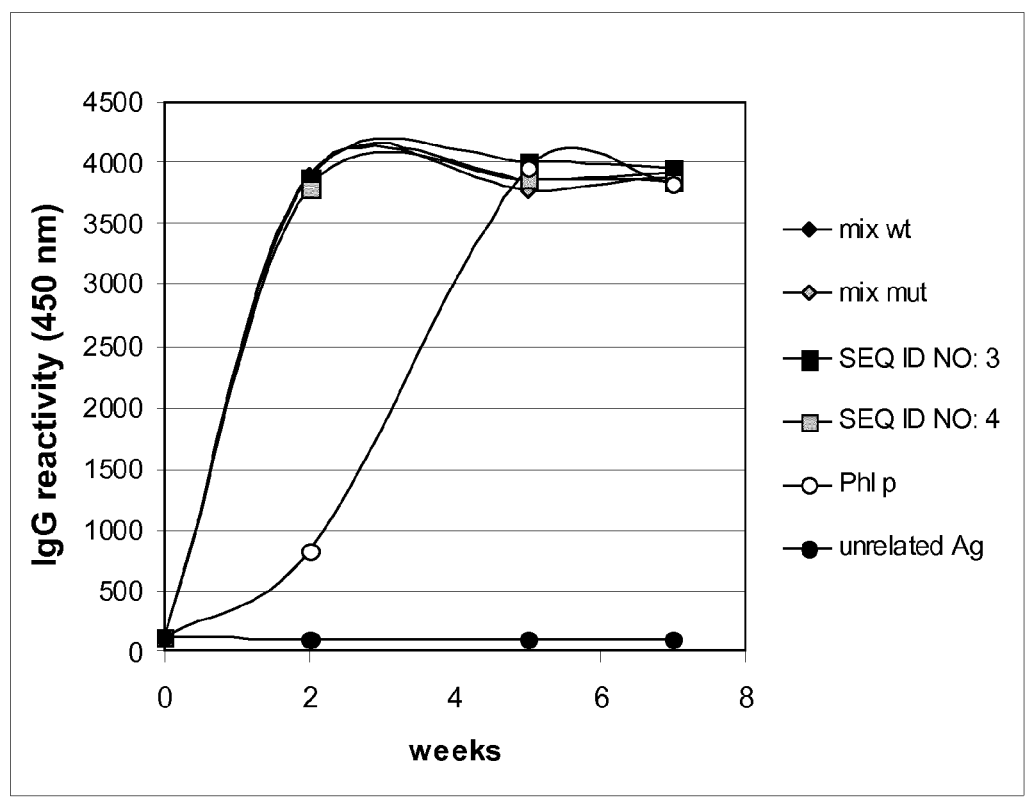
FIG. 12: Murine IgG response to SEQ ID NO: 1
Figure 13:
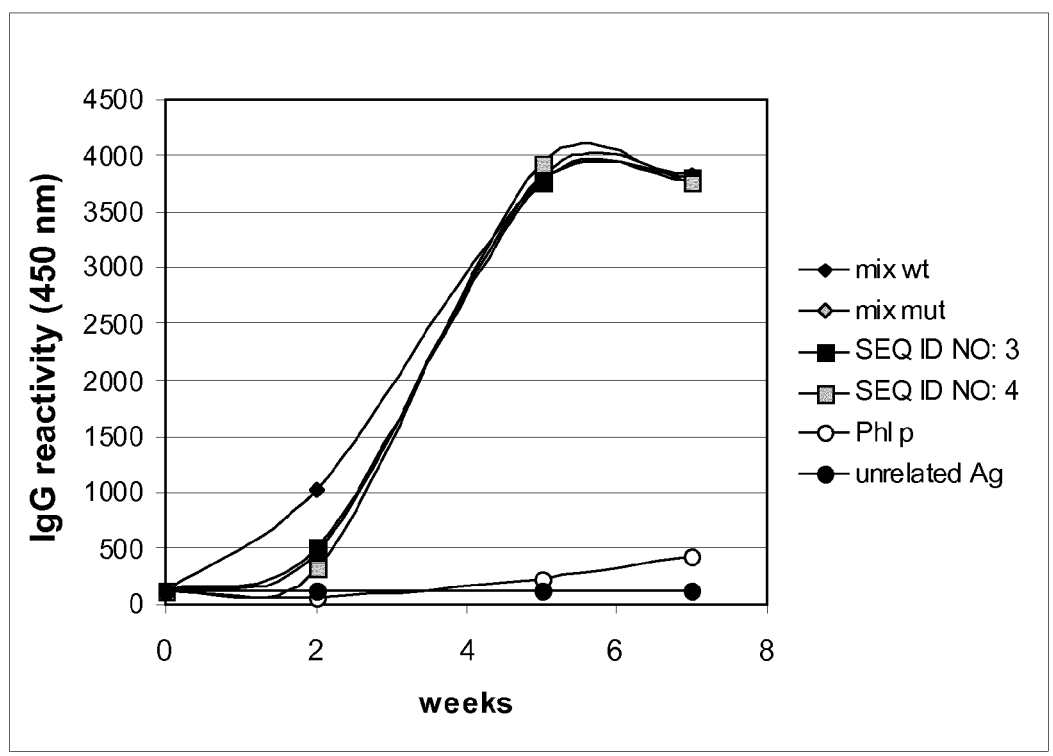
FIG. 13: Murine IgG response to Phl p 1
Figure 14:
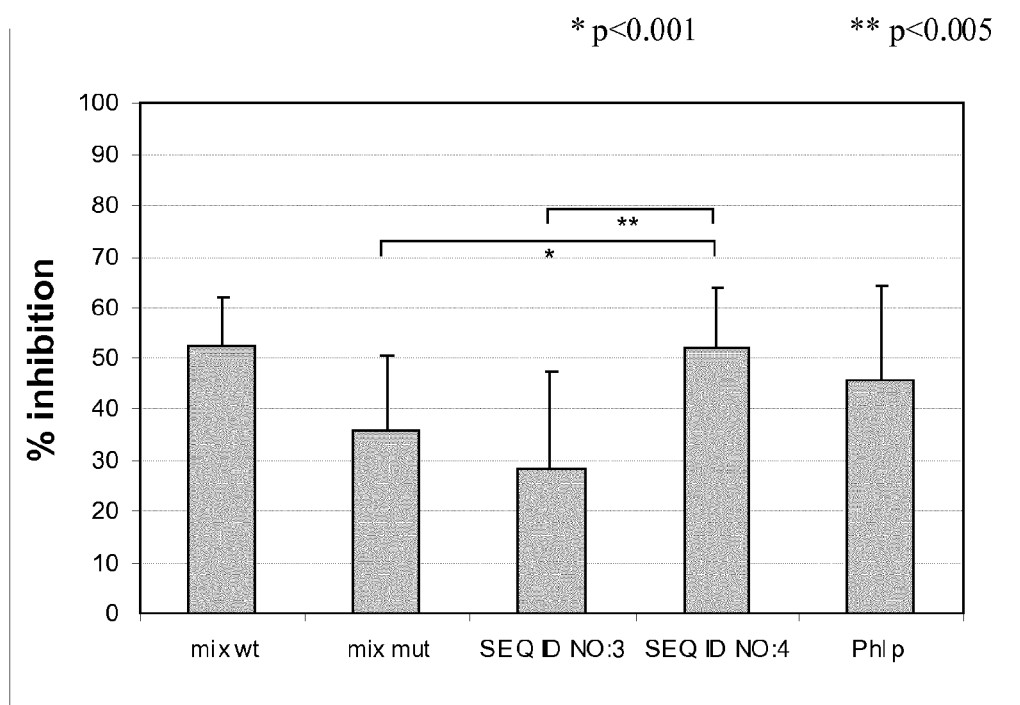
FIG. 14: Inhibition of IgE binding to Phl p by murine IgG antibodies

The amplification product obtained from Phl p 1 was re-amplified by replacing Php1 DIM Kpn FW con Phl p 1 DIM His FW (gcg ggtacccatatg cat cac cat cac cat cac atc ccc aag gtt ccc ccg SEQ ID NO:18), whereby a sequence coding for six histidines upstream of Phl p 1 sequence was inserted. A Kpn I site and a Nde I site (containing the ATG) were inserted at 5' of Phl p 1 amplification product, and a Eco R I site was inserted at its 3' in place of the stop codon. An Eco R I site was inserted in place of the ATG at 5' of Phl p 5, and a Bam H I site was inserted at its 3' after the stop codon. The amplified products were purified and digested with Kpn I and Eco R I restriction enzymes (Phl p 1), or Eco R I and Bam H I (Phl p 5) (restriction sites are underlined in the primers), and subsequently inserted into Kpn I/Bam H I sites of pEt 3c vector (Stratagene, La Jolla, Calif.) to obtain a construct capable of expressing a Phl p 1-Phl p 5 fusion protein preceded by a sequence of six histidines. Introduction of Eco R I restriction site, that is necessary for cloning of fragments, allowed for insertion of two amino acids (glutamic acid and phenylalanine) at the junction of the two proteins without altering the reading frame (FIG. 8).

Clones obtained from single bacterial colonies were sequenced by the Sanger method to verify that base change was correct, and the absence of unspecific mutations in the cDNA.

Example 3

Construction of a Plasmid Coding for Mutant Phl p 1-Phl p 5 Hybrid Molecule (MutHybrid)

The hybrid molecule coding for mutant Phl p 1-Phl p 5 hybrid was obtained following the method described in EXAMPLE 2 for the wild-type hybrid variant.

The oligonucleotide pairs used in the PCR reaction were identical, while the cDNAs used as templates encoded for two hypoallergenic variants whose sequences are herein identified as SEQ ID NO: 12 (for Phl p 1 mutant) and SEQ ID NO: 8 (Phl p 5 mutant).

Example 4

Production of Phl p 5 Proteins, Respective Mutants, wtHybrid and MutHybrid

Wild-type Phl p 1 (SEQ ID NO:11) and Phl p 5 (SEQ ID NO:7) cDNAs, mutagenized cDNAs (SEQ ID NO:12 and SEQ ID NO:8), and engineered wt and Mut Hybrid cDNAs (SEQ ID NO: 9 e 10), preceded by the sequence coding for six histidines, were cloned in an expression vector and expressed in *Escherichia coli* cells according to standard protocols. Cells were collected by centrifugation and resuspended in 100 mM $NaH_2PO_4$ buffer, pH 8 and lysed by sonication. The recombinant proteins were separated by centrifugation. Soluble Phl p 5 protein (SEQ ID NO: 1) was purified from the supernatant by affinity chromatography using Ni-NTA agarose columns bound to nitrilotriacetic acid (Qiagen, Milan, Italy) which chelates nickel ions interacting with the six-histidine portion fused to the allergen. Mutagenized Phl p 5 (SEQ ID NO: 2) and wt and mutant Hybrid (SEQ ID NO: 3 and 4), separated as aggregate in the pellet, were resuspended in denaturing buffer 8 M urea, 100 mM $NaH_2PO_4$, 10 mM Tris pH 8 and stirred for 60 min at 20° C. The solubilized recombinant proteins were separated from insoluble debris by centrifugation and purified from the supernatant under denaturing conditions by affinity chromatography using Ni-NTA agarose columns. Purified proteins were refolded by dialysis in a 5 mM $(NH_4)HCO_3$ solution for 18 hours at 4° C.

Example 5

Characteristics of Sera from Allergic Subjects

Sera were collected from subjects with a clinical history of seasonal allergy to *Phleum pratense* pollen, and high EAST reactivity specific for Phl p 1 and Phl p 5 allergens and used in single or pooled form. A pool of sera from non-allergic subjects was used as a negative control.

Example 6

ELISA Analysis of Phl p 5 Variants Reactivity to IgEs from a Serum Pool

Equivalent amounts (25 pmol) in 50 mM carbonate/bicarbonate buffer, pH 9.6 of wt allergen (SEQ ID NO: 1), mutagenized variant (SEQ ID NO:2) and unrelated antigen (BSA) were adsorbed on wells of polystirene plates for ELISA assay by incubation at 4° C. for 16 hours. The wells were washed with washing solution (60 mM phosphate buffer, pH 6.5, containing 0.05% Tween-20), and blocked with dilution solution (2% BSA in PBS 1x). 100 µl aliquots, diluted 1:5 in dilution buffer, of a pool of eleven human sera from EAST positive or non-allergic subjects (data not shown) were added to each sample and incubated at 25° C. for 2 hours. After three washes, peroxidase-conjugated anti human-IgE serum (1:4000 in diluting buffer) was added, followed by incubation at 25° C. for 1.5 hours. After three washes, the colorimetric reaction was developed by adding 100 µl of TMB reagent (BioFX Laboratories, Owings Mills, Md.) and incubating for 15 minutes at 25° C. The reaction was stopped by adding 100 µl of 1 N HCl and read at 450 nm using a microplate reader spectrophotometer. Results were confirmed by three independent experiments.

The same protocol was applied with some modifications to test IgE reactivity of the engineered wt and Mut hybrids. Serial dilution of the hybrid allergens (SEQ ID NO:3 and 4) were prepared in a 1:2 ratio, starting from 0.4 nmol/ml and adsorbed on wells of polystirene plates. A pool of sera positive to *Phleum pratense* pollen was diluted 1:8 in diluting solution.

Example 7

ELISA Inhibition Assay—Monomeric Variant SEQ ID NO: 2 Ability to Inhibit Binding of Phl p 5 to IgEs in Serum Equal amounts (1.25 pmol) of wild type Phl p 5 (SEQ ID NO: 1), in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6,5, containing 0.05% Tween-20), and free sites were blocked with diluting solution (2% BSA, PBS 1x). Aliquots (100 µl) of a 1:10 dilution of pooled human sera positive to Phl p 5 were pre-incubated with two-fold serial dilutions of wt or mutagenized allergens starting from 25 pmol/ml at 25° C. for 2 hours. The mixes were then added to each well, and incubated at 4° C. for 16 hours. After three washes, anti-human IgE peroxidase-conjugated serum diluted 1:4000 in diluting buffer was added, and incubated at 25° C. for 1.5 hours. Colorimetric reaction development was obtained by adding 100 µl TMB reagent and incubating for 15 minutes at 25° C. The reaction was stopped by adding 100 µl 1 N HCl, and evaluated by reading at 450 nm with a spectrophotometer. Inhibition percentage was calculated by using the following formula: $100 \times [(A-B)/A]$, where A is absorbance at 450 nm in the absence of inhibitor, and B is absorbance in the presence of inhibitor. Data are representative of three independent experiments.

Example 8

ELISA Inhibition Assay—Ability of SEQ ID NO: 3 and SEQ ID NO: 4 to Inhibit Binding of Human Serum IgEs to Phl p Pollen Extract or Phl p 1 and Phl p 5 Mix Equal amounts (0.05 µg) of *Phleum pratense*, in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6,5, containing 0.05% Tween-20), and free sites were blocked with diluting solution (2% BSA in PBS 1x). Aliquots (70 µl) of a 1:10 dilution of a pool of human sera positive to *Phleum pratense* pollen were pre-incubated with equimolar amounts (150 nmol/ml) of wild type allergen, mutagenized or engineered variants (hybrids) or 0.5 µg/ml of *Phleum pratense* pollen extract at 25° C. for 2 hours. The mixes were then added to each well, and incubated at 4° C. for 16 hours. After three washes, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent and incubating for 15 minutes at 25° C. The reaction was stopped by adding 100 µl 1 N HCl, and evaluated by reading at 450 nm with a spectrophotometer. Inhibition percentage was calculated by using the following formula: $100 \times [(A-B)/A]$, where A is absorbance at 450 nm in the absence of inhibitor, and B is absorbance in the presence of inhibitor.

To test the ability of wt and mutagenised hybrid proteins, SEQ ID NO: 3 and 4, to inhibit Phl p 1 and Phl p 5 mix, the same protocol was applied with the following modifications: the amount of protein adsorbed on wells was 12.5 pmol of Phl p 1 and Phl p 5, the inhibitor concentration started from 0.1 nmol/ml (two-fold serial dilution), the dilution of the pool of sera positive to *Phleum pratense* was 1:10.

TABLE 2

Hybrid wild-type- and mutagenized-molecules inhibit IgE binding to *Phleum pratense* pollen extract

| serum | *Phleum pratense* | wt Mix | Mut Mix | SEQ ID NO: 3 | SEQ ID NO: 4 |
|---|---|---|---|---|---|
| 1 | 74.7 | 57.6 | 53 | 67.7 | 49.9 |
| 2 | 74.5 | 13.7 | 6.3 | 16.9 | 13.2 |
| 3 | 82.2 | 43.3 | 25 | 50.9 | 41.2 |
| 4 | 78.8 | 16.7 | 10 | 18.9 | 12.5 |
| 5 | 79.1 | 59.2 | 56.6 | 68.1 | 54.5 |
| 6 | 87.5 | 81.1 | 60.4 | 87.9 | 75.8 |
| 7 | 91.3 | 52.4 | 30.3 | 53.4 | 39 |
| 8 | 78.9 | 67.8 | 53.8 | 69.6 | 63.7 |
| 9 | 28 | 62.9 | 39.6 | 60.4 | 51.6 |
| 10 | 41.6 | 54.9 | 16.3 | 49.3 | 43.2 |
| Mean % inhibition | 71.7 | 51.0 | 35.1 | 54.3 | 44.5 |
| Standard deviation | 20.4 | 21.3 | 20.4 | 22.3 | 19.9 |

Example 9

Immunization of Balb/c Mice

Seven groups of mice each composed of five Balb/c strain female animals (Charles River) were subcutaneously immunized with 150 pmol of wt, mutagenized or engineered (hybrid) allergen or 10 µg of *Phleum pratense* pollen extract mixed with 2 mg of $Al(OH)_3$) in 200 µl saline. Other two boosts were performed after 21 and 42 days. As a control, five mice received the same treatment with an unrelated antigen. Two, five and seven weeks following first immunization, blood collection was performed from jugular vein of mice, and antibody response to the respective immunogen, wt molecules and *Phleum pratense* pollen extract was checked by ELISA. Sera from mice were tested singularly or pooled based on immunogenic type and time elapsed from first immunization.

Example 10

ELISA Analysis of Specific Murine IgG Response

Figure 1:
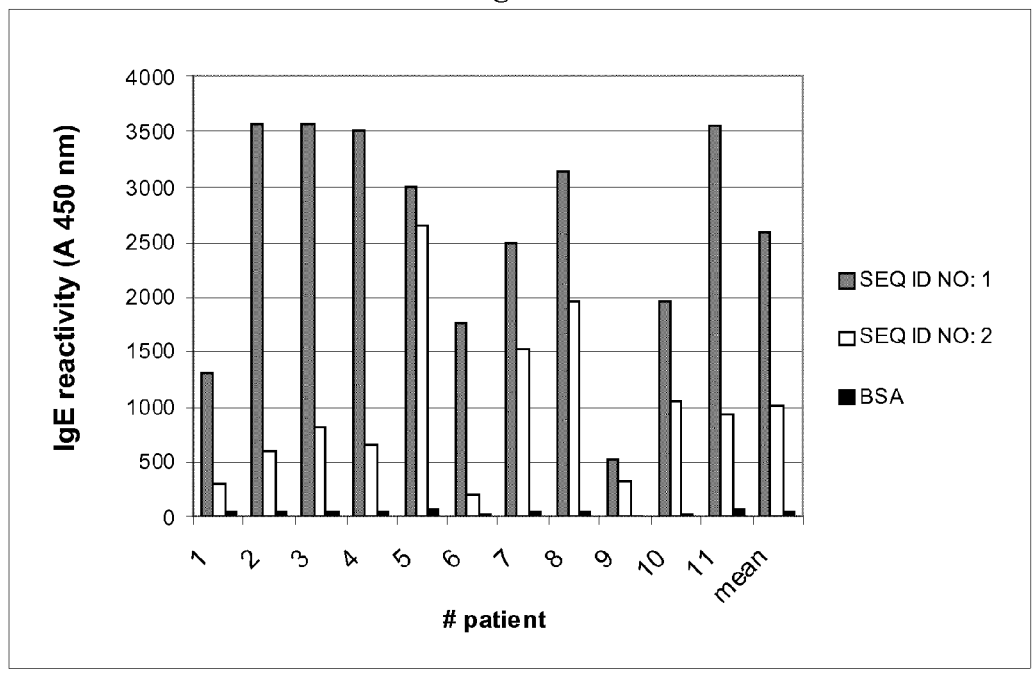
FIG. 1: ELISA analysis of IgE reactivity to Phl p 5 allergen and its hypoallergenic variant SEQ ID NO: 2
Figure 2:
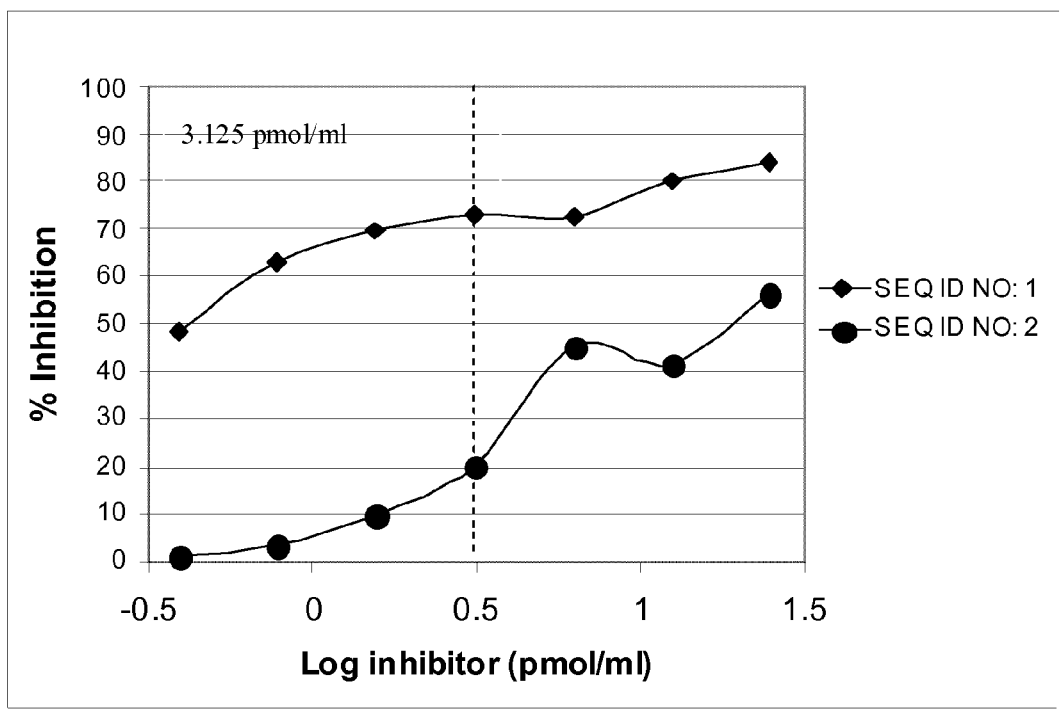
FIG. 2: Inhibition of IgE binding to Phl p 5 allergen
Figure 3:
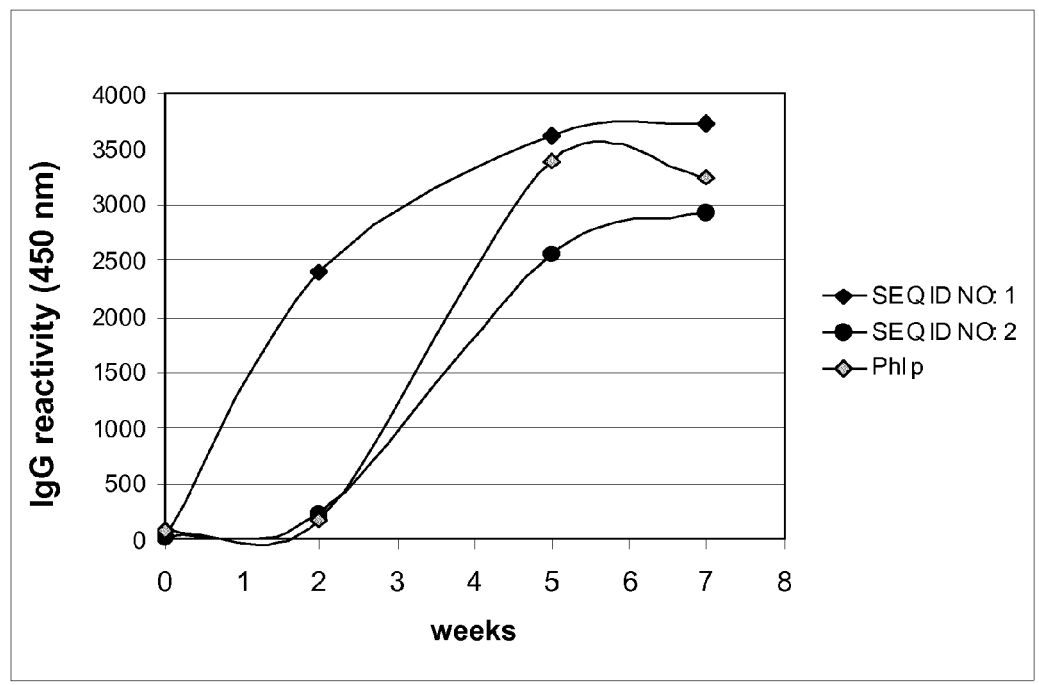
FIG. 3: Murine IgG response to respective immunogenic proteins
Figure 4:
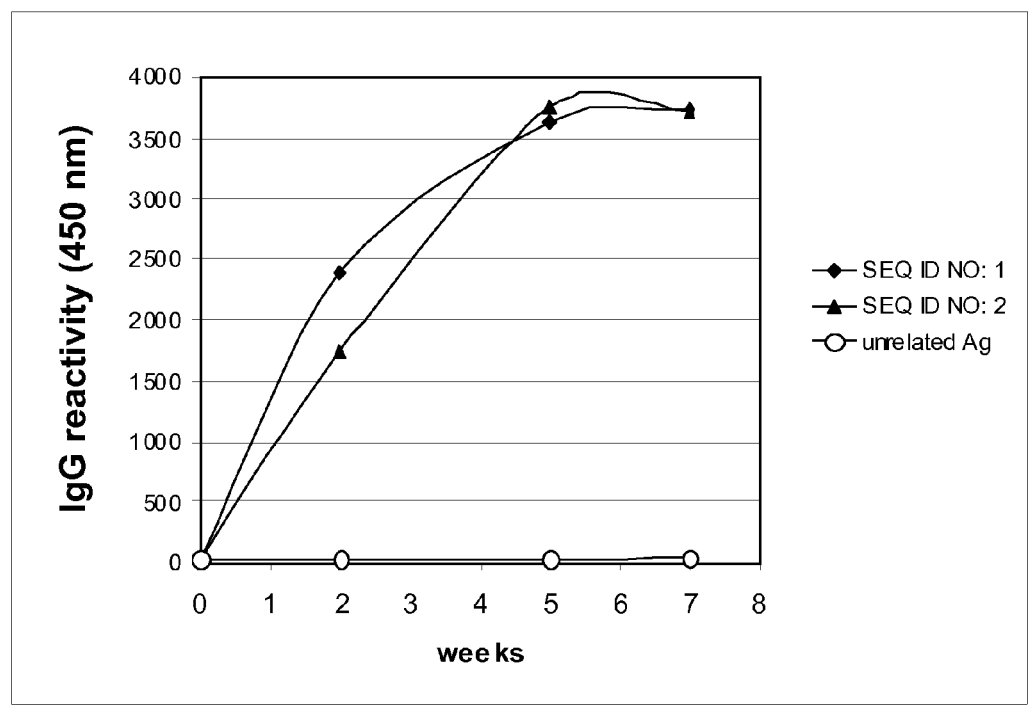
FIG. 4: IgG response in mice immunised with SEQ ID NO:1
Figure 5:
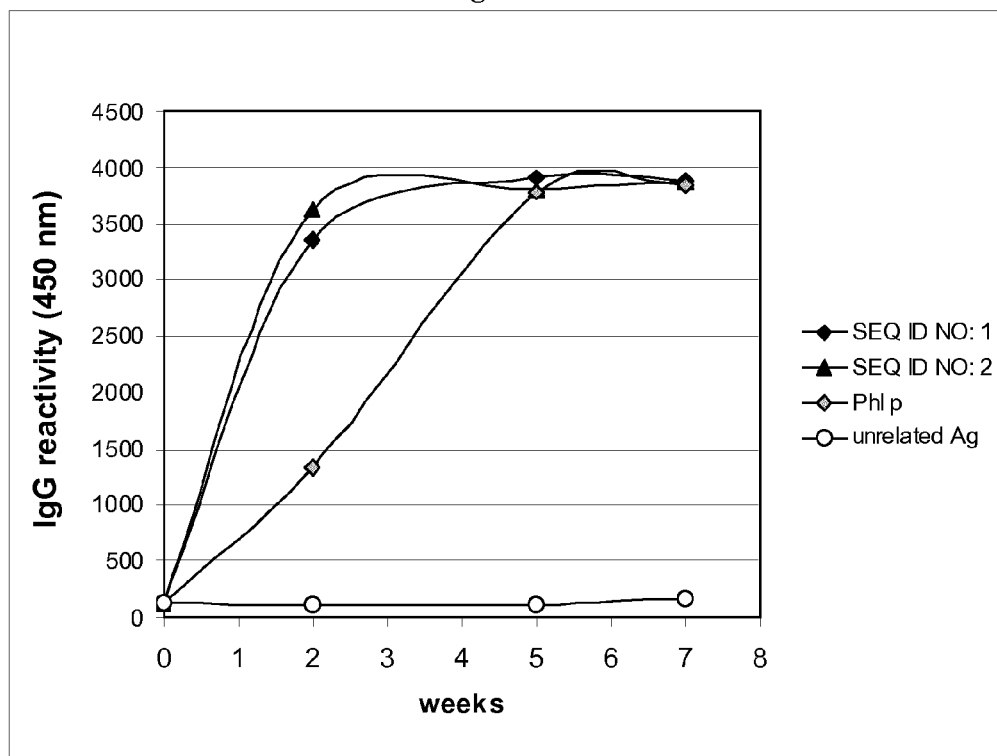
FIG. 5: Murine IgG response to Phl p pollen extract.
Figure 6:
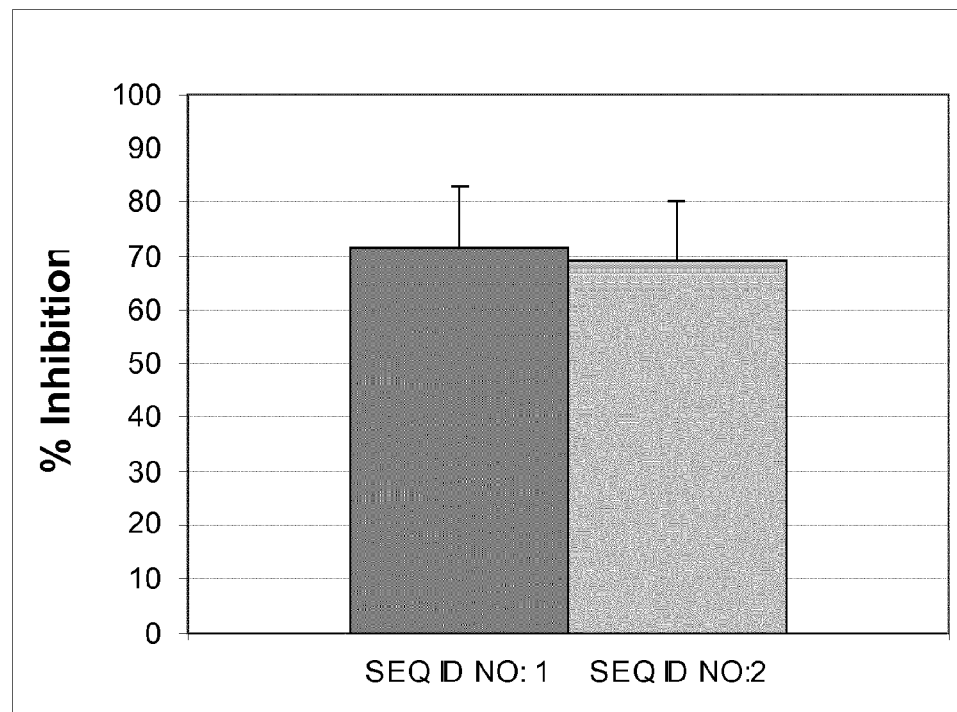
FIG. 6: Inhibition of IgE binding to SEQ ID NO: 1 by murine IgG antibodies
Figure 7:
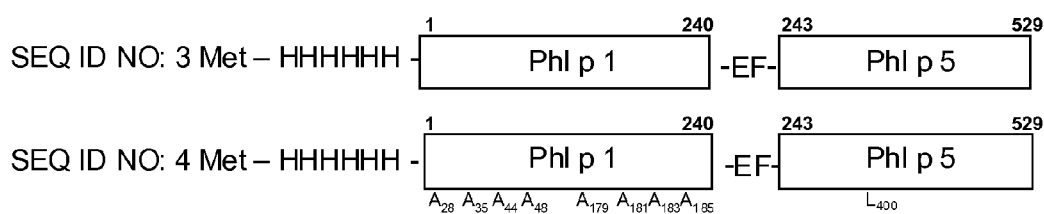
FIG. 7: Schematic presentation of hybrid protein SEQ ID NO: 3 and SEQ ID NO: 4

Equal amounts of *Phleum pratense* pollen extract (20 µg/ml), wt Phl p 5 or Phl p 1, SEQ ID NO: 2 and SEQ ID NO: 4 variants (2 µg/ml), in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6,5, containing 0.05% Tween-20), and free sites were blocked with diluting solution (2% BSA in PBS 1×). Equal aliquots (100 µl) of each mouse serum or pooled sera were added to each well at a 1:1000 (FIG. 5) or 1:5000 dilution in diluting buffer, and incubated at 25° C. for 2 hours. After three washes, anti-total mouse IgG peroxidase-conjugated serum diluted 1:8000 in diluting buffer was added and incubated at 25° C. for 1.5 hours. After three washes, colorimetric reaction development was obtained by adding 100 µl TMB reagent and incubating for 20 minutes at 25° C. The reaction was stopped by adding 100 µl 1 N HCl and read at 450 nm with a spectrophotometer. Data show the mean reactivity obtained by analysis of the sera from 5 mice for each group.

Example 11

ELISA Inhibition Assay. IgGs Against SEQ ID NO: 2 and SEQ ID NO: 4 Inhibit Binding Between *Phleum pratense* Pollen Extract and IgEs in the Sera of Allergic Patients Positive to *Phleum pratense*

Equal amounts of *Phleum pratense* pollen extract (1 µg) in 50 mM carbonate/bicarbonate buffer, pH 9.6, were adsorbed onto wells of polystyrene plates for ELISA assay by incubating at 4° C. for 16 hours. Wells were then washed with washing solution (60 mM phosphate buffer, pH 6,5, containing 0.05% Tween-20), and free sites were blocked with diluting solution (BSA 2%, PBS 1×). Aliquots (100 µl) of 1:15 diluted pools from mouse sera collected after seven weeks from first immunization were incubated at 4° C. for 16 hours. After three washes, seven 1:10 diluted human sera positive to *Phleum pratense* were added at 4° C. for 16 hours. After three washes, anti-human IgE peroxidase-conjugated serum diluted 1:4000 in diluting buffer was added, and incubated at 25° C. for 1.5 hours. After three washes, colorimetric reaction development was obtained by adding 100 µl TMB reagent (BioFX Laboratories, Owings Mills, Md.), and incubating for 20 minutes at 25° C. The reaction was stopped by adding 100 µl 1 N HCl and read at 450 nm with a spectrophotometer. Inhibition percentage was calculated by using the following formula: $100 \times [(A-B)/A]$, where A is absorbance at 450 nm when antigen is pre-incubated with serum from not-immunized mice, and B is absorbance in the presence of serum from immunized mice.

Example 12

Statistical Analysis

In the figures, results are expressed as mean values plus corresponding standard deviations.
UNISTAT 5.5 Light for Excel software was used for statistical analyses. Data were analyzed by paired t-Test.

BIBLIOGRAPHY

1. Vrtala S, (2008) "From allergen genes to new forms of allergy diagnosis and treatment". Allergy; 63(3):299-309.
2. Toubi E., Kessel A., Blant A., Golan T. D., (1999) "Follow-up after systemic adverse reactions of immunotherapy". Allergy; 54(6):617-620.
3. Vrtala S, Ball T, Spitzauer s, Pandjaitan B, Suphioglu C, Knox B, Sperr W R, Valent P, Kraft D, Valenta R. (1998). "Immunization with purified natural and recombinant allergens induces mouse IgG1 antibodies that recognize similar epitopes as human IgE and inhibit the human IgE-allergen interaction and allergen-induced basophil degranulation". J Immunol; 160:6137.
4. Andersson K, Lidholm J. (2003). "Characteristics and immunobiology of grass pollen allergens". Int Arch Allergy Immunol; 130:87-107.
5. Dahl R, Stender A, Rak S. (2006). "Specific immunotherapy with SQ standardized grass allergen tablets in asthmatics with rhinoconjunctivitis". Allergy; 61:185-190.
6. Hejl C, Wurtzen P A, Kleine-Tebbe J, Johansen N, Broge L, Ipsen H. (2009) "*Phleum pratense* alone is sufficient for allergen-specific immunotherapy against allergy to Poideae grass pollens". Clin Exp Allergy; 39(5):752-759.

7. Becker W M, Bufe A, Petersen A, Schlaak M. (1995). "Molecular characterization of timothy grass pollen group V allergens" Int Arch Allergy Immunol. 107(1-3):242-4.
8. Bufe A, Becker W M, Schramm G, Petersen A, Mamat U, Schlaak M. (1994) "Major allergen Phl p Va (Timothy grass) bears at least two different IgE-reactive epitome". J Allergy Clin Immunol; 94:173-181.
9. Cromwell O, Hafner D, Nandy A. (2011). "Recombinant allergens for specific immunotherapy" J Allergy Clin Immunol; 127(4):865-872.
10. Gehlar K, Rajashankar K R, Hofmann E, Betzel C, Weber W, Werner S, Bufe A. (2006) "Lysine as a critical amino acid for IgE binding in Phl p 5b C terminus". Int Arch Allergy Immunol; 140:285-294.
11. Schramm G, Kahlert H, Suck R, Weber B, Stuwe H T, Muller W D, Bufe A, Becker W M, Schlaak M W, Jager L, Cromwell 0, Fiebig H. (1999). "Allergen engineering: variants of the Timothy grass pollen allergen Phl p 5b with reduced IgE-binding capacity but conserved T cell reactivity". The Journal of Immunology; 162:2406-2414.
12. Wald M, Kahlert H, Weber B, Jankovic M, Keller W, Cromwell 0, Nandy A, Fiebig H. (2007). "Generation of a low immunoglobulin E-binding mutant of the timothy grass pollen major allergen Phl p 5a". Clin Exp Allergy; 37(3):441-50.
13. Maglio O, Saldanha J W, Vrtala S, Spitzauer S, Valenta R, Pastore A. (2002) "A major IgE epitope-containing grass pollen allergen domani from Phl p 5 folds as a four-helix bundle" Protein Engineering; 15:635-642.
14. Swoboda I, De Weerd N, Bhalla P L, Niederberger V, Sperr W R, Valent P, Kahlert H, Fiebig H, Verdino P, Keller W, Ebner C, Spitzauer S, Valenta R, Singh M B. (2002) "Mutants of the major ryegrass pollen allergen, Lol p 5, with reduced IgE-binding capacity: candidates for grass pollen-specific immunotherapy". Eur J Immunol; 32(1):270-80.
15. Linhart B, Mothes-Luksch N, Vrtala S, Kneidinger M, Valent P, Valenta R. (2008). "A hypoallergenic hybrid molecule with increased immunogenicity consisting of derivatives of the major grass pollen allergens, Phl p 2 and Phl p 6". Biol Chem; 389(7):925-33.
16. Linhart B, Hartl A, Jahn-Schmid B, Verdino P, Keller W, Krauth M T, Valent P, Horak F, Wiedermann U, Thalhamer J, Ebner C, Kraft D, Valenta R. (2005). "A hybrid molecule resembling the epitope spectrum of grass pollen for allergy vaccination" J Allergy Clin Immunol.; 115(5): 1010-6.
17. Metz-Favre C, Linhart B, Focke-Tejkl M, Purohit A, de Blay F, Valenta R, Pauli G. (2007) "Skin test diagnosis of grass pollen allergy with a recombinant hybrid molecule"; J Allergy Clin Immunol; 120(2):315-21.
18. Wild C, Wallner M, Hufnagl K, Fuchs H, Hoffmann-Sommergruber K, Breiteneder H, Scheiner O, Ferreira F, Wiedermann U. (2007) "A recombinant allergen chimera as novel mucosal vaccine candidate for prevention of multi-sensitivities". Allergy; 62:33-41.
19. Wang W., Malcolm B A. (2002). "Two-stage polymerase chain reaction protocol allowing introduction of multiple mutations, deletions, and insertions, using QuikChange site-directed mutagenesis". Methods Mol Biol.; 182: 37-43.
20. Paul. (1989), "Fundamental Immunology", Raven press, New York. Sostituire Cryz,
21. Anhoj C., Backer V., Nolte H. (2001). "Diagnostic evaluation of grass- and birch-allergic patients with oral allergy syndrome". Allergy; 56(6):548-

The invention claimed is:

1. A hybrid protein containing a hypoallergenic sequence variant of the Phl p 5 major allergen from *Phleum pratense* pollen consisting of SEQ ID NO:2 and a hypoallergenic sequence variant of the major allergen Phl p 1 from *Phleum pratense* pollen consisting of SEQ ID NO: 6.

2. The hybrid protein according to claim 1, wherein said Phl p 1 and Phl p 5 hypoallergenic sequence variants are located at either amino or carboxyl ends with a head-to-tail orientation.

3. The hybrid protein according to claim 2, wherein said Phl p 1 and Phl p 5 are located at the amino- and carboxyl-end, respectively.

4. The hybrid protein of claim 1, wherein said sequence variant of the Phl p 5 major allergen and the hypoallergenic variant of the major allergen Phl p 1 are separated by a linker.

5. The hybrid protein of claim 4, wherein said linker consists of EF dipeptide.

6. The hybrid protein according to claim 4, wherein said linker consists of an amino acid sequence containing from 1 to 8 amino acids.

7. The hybrid protein according to claim 6, consisting of SEQ ID NO:4.

8. A pharmaceutical composition containing an effective amount of a hybrid protein according to claim 1, and pharmaceutically acceptable carriers, excipients or adjuvants.

9. The composition according to claim 8, which is in a form suitable for sublingual, intranasal, subcutaneous or transdermal administration.

10. A method of treating patients allergic to *Phleum pratense* pollen comprising:

administering to said patients in need thereof an effective amount of a hybrid protein according to claim 1 or a pharmaceutical composition thereof.

11. The method of claim 10, wherein said patients have bronchial asthma, allergic rhinitis, allergic conjunctivitis, or allergic oral syndrome.

12. A nucleic acid molecule coding for a hybrid protein according to claim 1.

13. A nucleic acid molecule according to claim 12, whose sequence is selected from SEQ ID NO:8 and 10.

14. An expression vector containing the nucleic acid molecule according to claim 12.

* * * * *

SEQUENCE LISTING

```
<160> NUMBER OF SEQ ID NOS: 18

<210> SEQ ID NO 1
<211> LENGTH: 287
<212> TYPE: PRT
<213> ORGANISM: Phleum pratense

<400> SEQUENCE: 1

Ala Asp Leu Gly Tyr Gly Pro Ala Thr Pro Ala Ala Pro Val Ala Gly
1               5                   10                  15

Tyr Thr Pro Ala Thr Pro Ala Ala Pro Ala Gly Ala Glu Pro Ala Gly
            20                  25                  30

Lys Ala Thr Thr Glu Glu Gln Lys Leu Ile Glu Lys Ile Asn Ala Gly
        35                  40                  45

Phe Lys Ala Ala Leu Ala Ala Ala Gly Val Pro Pro Ala Asp Lys
    50                  55                  60

Tyr Arg Thr Phe Val Ala Thr Phe Gly Ala Ala Ser Asn Lys Ala Phe
65                  70                  75                  80

Ala Glu Gly Leu Ser Gly Glu Pro Lys Gly Ala Ala Glu Ser Ser Ser
                85                  90                  95

Lys Ala Ala Leu Thr Ser Lys Leu Asp Ala Ala Tyr Lys Leu Ala Tyr
                100                 105                 110

Lys Thr Ala Glu Gly Ala Thr Pro Glu Ala Lys Tyr Asp Ala Tyr Val
            115                 120                 125

Ala Thr Leu Ser Glu Ala Leu Arg Ile Ile Ala Gly Thr Leu Glu Val
        130                 135                 140
```

His Ala Val Lys Pro Ala Glu Glu Val Lys Val Ile Pro Ala Gly
145                 150                 155                 160

Glu Leu Gln Val Ile Glu Lys Val Asp Ala Ala Phe Lys Val Ala Ala
            165                 170                 175

Thr Ala Ala Asn Ala Ala Pro Ala Asn Asp Lys Phe Thr Val Phe Glu
            180                 185                 190

Ala Ala Phe Ser Asn Ala Ile Lys Ala Ser Thr Gly Gly Ala Tyr Glu
            195                 200                 205

Ser Tyr Lys Phe Ile Pro Ala Leu Glu Ala Ala Val Lys Gln Ala Tyr
210                 215                 220

Ala Ala Thr Val Ala Thr Ala Pro Glu Val Lys Tyr Thr Val Phe Glu
225                 230                 235                 240

Thr Ala Leu Lys Lys Ala Ile Thr Ala Met Ser Glu Ala Gln Lys Ala
            245                 250                 255

Ala Lys Pro Ala Ala Ala Ala Thr Ala Thr Ala Thr Ser Ala Val Gly
            260                 265                 270

Ala Ala Ala Gly Ala Ala Thr Ala Ala Thr Gly Gly Tyr Lys Val
            275                 280                 285

<210> SEQ ID NO 2
<211> LENGTH: 287
<212> TYPE: PRT
<213> ORGANISM: Unknown
<220> FEATURE:
<223> OTHER INFORMATION: Phl p 5 mutant

<400> SEQUENCE: 2

Ala Asp Leu Gly Tyr Gly Pro Ala Thr Pro Ala Ala Pro Val Ala Gly
1               5                   10                  15

Tyr Thr Pro Ala Thr Pro Ala Ala Pro Ala Gly Ala Glu Pro Ala Gly
            20                  25                  30

Lys Ala Thr Thr Glu Glu Gln Lys Leu Ile Glu Lys Ile Asn Ala Gly
            35                  40                  45

Phe Lys Ala Ala Leu Ala Ala Ala Ala Gly Val Pro Pro Ala Asp Lys
50                  55                  60

Tyr Arg Thr Phe Val Ala Thr Phe Gly Ala Ala Ser Asn Lys Ala Phe
65                  70                  75                  80

Ala Glu Gly Leu Ser Gly Glu Pro Lys Gly Ala Ala Glu Ser Ser Ser
            85                  90                  95

Lys Ala Ala Leu Thr Ser Lys Leu Asp Ala Ala Tyr Lys Leu Ala Tyr
            100                 105                 110

Lys Thr Ala Glu Gly Ala Thr Pro Glu Ala Lys Tyr Asp Ala Tyr Val
            115                 120                 125

Ala Thr Leu Ser Glu Ala Leu Arg Ile Ile Ala Gly Thr Leu Glu Val
130                 135                 140

His Ala Val Lys Pro Ala Ala Glu Glu Val Lys Val Ile Leu Ala Gly
145                 150                 155                 160

Glu Leu Gln Val Ile Glu Lys Val Asp Ala Ala Phe Lys Val Ala Ala
            165                 170                 175

Thr Ala Ala Asn Ala Ala Pro Ala Asn Asp Lys Phe Thr Val Phe Glu
            180                 185                 190

Ala Ala Phe Ser Asn Ala Ile Lys Ala Ser Thr Gly Gly Ala Tyr Glu
            195                 200                 205

Ser Tyr Lys Phe Ile Pro Ala Leu Glu Ala Ala Val Lys Gln Ala Tyr
210                 215                 220

```
Ala Ala Thr Val Ala Thr Ala Pro Glu Val Lys Tyr Thr Val Phe Glu
        225             230             235             240

Thr Ala Leu Lys Lys Ala Ile Thr Ala Met Ser Glu Ala Gln Lys Ala
                245             250             255

Ala Lys Pro Ala Ala Ala Thr Ala Thr Thr Ser Ala Val Gly
        260             265             270

Ala Ala Ala Gly Ala Ala Thr Ala Ala Thr Gly Gly Tyr Lys Val
        275             280             285

<210> SEQ ID NO 3
<211> LENGTH: 529
<212> TYPE: PRT
<213> ORGANISM: Unknown
<220> FEATURE:
<223> OTHER INFORMATION: Phl p 1 - Phl p 5 hybrid wt

<400> SEQUENCE: 3

Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Lys Pro Thr Gly Ala
            20                  25                  30

Gly Pro L

-continued

```
Asp Lys Tyr Arg Thr Phe Val Ala Thr Phe Gly Ala Ala Ser Asn Lys
305                 310                 315                 320

Ala Phe Ala Glu Gly Leu Ser Gly Glu Pro Lys Gly Ala Ala Glu Ser
            325                 330                 335

Ser Ser Lys Ala Ala Leu Thr Ser Lys Leu Asp Ala Ala Tyr Lys Leu
        340                 345                 350

Ala Tyr Lys Thr Ala Glu Gly Ala Thr Pro Glu Ala Lys Tyr Asp Ala
    355                 360                 365

Tyr Val Ala Thr Leu Ser Glu Ala Leu Arg Ile Ile Ala Gly Thr Leu
370                 375                 380

Glu Val His Ala Val Lys Pro Ala Ala Glu Glu Val Lys Val Ile Pro
385                 390                 395                 400

Ala Gly Glu Leu Gln Val Ile Glu Lys Val Asp Ala Ala Phe Lys Val
            405                 410                 415

Ala Ala Thr Ala Ala Asn Ala Ala Pro Ala Asn Asp Lys Phe Thr Val
        420                 425                 430

Phe Glu Ala Ala Phe Ser Asn Ala Ile Lys Ala Ser Thr Gly Gly Ala
    435                 440                 445

Tyr Glu Ser Tyr Lys Phe Ile Pro Ala Leu Glu Ala Ala Val Lys Gln
450                 455                 460

Ala Tyr Ala Ala Thr Val Ala Thr Ala Pro Glu Val Lys Tyr Thr Val
465                 470                 475                 480

Phe Glu Thr Ala Leu Lys Lys Ala Ile Thr Ala Met Ser Glu Ala Gln
            485                 490                 495

Lys Ala Ala Lys Pro Ala Ala Ala Ala Thr Ala Thr Ala Thr Ser Ala
        500                 505                 510

Val Gly Ala Ala Gly Ala Ala Thr Ala Ala Thr Gly Gly Tyr Lys
    515                 520                 525

Val
```

```
<210> SEQ ID NO 4
<211> LENGTH: 529
<212> TYPE: PRT
<213> ORGANISM: Unknown
<220> FEATURE:
<223> OTHER INFORMATION: Phl p 1 - Phl p 5 hybrid mutant

<400> SEQUENCE: 4
```

```
Ile Pro Lys Val Pro Pro Gly Pro Asn Ile Thr Ala Thr Tyr Gly Asp
1               5                   10                  15

Lys Trp Leu Asp Ala Lys Ser Thr Trp Tyr Gly Ala Pro Thr Gly Ala
            20                  25                  30

Gly Pro Ala Asp Asn Gly Gly Ala Cys Gly Tyr Ala Asp Val Asp Ala
        35                  40                  45

Pro Pro Phe Ser Gly Met Thr Gly Cys Gly Asn Thr Pro Ile Phe Lys
    50                  55                  60

Ser Gly Arg Gly Cys Gly Ser Cys Phe Glu Ile Lys Cys Thr Lys Pro
65                  70                  75                  80

Glu Ala Cys Ser Gly Glu Pro Val Val Val His Ile Thr Asp Asp Asn
                85                  90                  95

Glu Glu Pro Ile Ala Pro Tyr His Phe Asp Leu Ser Gly His Ala Phe
            100                 105                 110

Gly Ala Met Ala Lys Lys Gly Asp Glu Gln Lys Leu Arg Ser Ala Gly
        115                 120                 125

Glu Leu Glu Leu Gln Phe Arg Arg Val Lys Cys Lys Tyr Pro Glu Gly
```

```
                    130                 135                 140
Thr Lys Val Thr Phe His Val Glu Lys Gly Ser Asn Pro Asn Tyr Leu
145                 150                 155                 160

Ala Leu Leu Val Lys Tyr Val Asn Gly Asp Gly Asp Val Val Ala Val
                165                 170                 175

Asp Ile Ala Glu Ala Gly Ala Asp Ala Trp Ile Glu Leu Lys Glu Ser
                180                 185                 190

Trp Gly Ala Ile Trp Arg Ile Asp Thr Pro Asp Lys Leu Thr Gly Pro
                195                 200                 205

Phe Thr Val Arg Tyr Thr Thr Glu Gly Gly Thr Lys Thr Glu Ala Glu
                210                 215                 220

Asp Val Ile Pro Glu Gly Trp Lys Ala Asp Thr Ser Tyr Ser Ser Lys
225                 230                 235                 240

Glu Phe Ala Asp Leu Gly Tyr Gly Pro Ala Thr Pro Ala Ala Pro Val
                245                 250                 255

Ala Gly Tyr Thr Pro Ala Thr Pro Ala Ala Pro Ala Gly Ala Glu Pro
                260                 265                 270

Ala Gly Lys Ala Thr Thr Glu Glu Gln Lys Leu Ile Glu Lys Ile Asn
                275                 280                 285

Ala Gly Phe Lys Ala Ala Leu Ala Ala Ala Gly Val Pro Pro Ala
                290                 295                 300

Asp Lys Tyr Arg Thr Phe Val Ala Thr Phe Gly Ala Ala Ser Asn Lys
305                 310                 315                 320

Ala Phe Ala Glu Gly Leu Ser Gly Glu Pro Lys Gly Ala Ala Glu Ser
                325                 330                 335

Ser Ser Lys Ala Ala Leu Thr Ser Lys Leu Asp Ala Ala Tyr Lys Leu
                340                 345                 350

Ala Tyr Lys Thr Ala Glu Gly Ala Thr Pro Glu Ala Lys Tyr Asp Ala
                355                 360                 365

Tyr Val Ala Thr Leu Ser Glu Ala Leu Arg Ile Ile Ala Gly Thr Leu
                370                 375                 380

Glu Val His Ala Val Lys Pro Ala Ala Glu Glu Val Lys Val Ile Leu
385                 390                 395                 400

Ala Gly Glu Leu Gln Val Ile Glu Lys Val Asp Ala Ala Phe Lys Val
                405                 410                 415

Ala Ala Thr Ala Ala Asn Ala Ala Pro Ala Asn Asp Lys Phe Thr Val
                420                 425                 430

Phe Glu Ala Ala Phe Ser Asn Ala Ile Lys Ala Ser Thr Gly Gly Ala
                435                 440                 445

Tyr Glu Ser Tyr Lys Phe Ile Pro Ala Leu Glu Ala Ala Val Lys Gln
                450                 455                 460

Ala Tyr Ala Ala Thr Val Ala Thr Ala Pro Glu Val Lys Tyr Thr Val
465                 470                 475                 480

Phe Glu Thr Ala Leu Lys Lys Ala Ile Thr Ala Met Ser Glu Ala Gln
                485                 490                 495

Lys Ala Ala Lys Pro Ala Ala Ala Thr Ala Thr Ala Thr Ser Ala
                500                 505                 510

Val Gly Ala Ala Ala Gly Ala Ala Thr Ala Ala Thr Gly Gly Tyr Lys
                515                 520                 525

Val

<210> SEQ ID NO 5
<211> LENGTH: 240
```

<212> TYPE: PRT
<213> ORGANISM: Phleum pratense

<400> SEQUENCE: 5

```
Ile Pro Lys Val Pro Pro Gly Pro Asn Ile Thr Ala Thr Tyr Gly Asp
1               5                   10                  15
Lys Trp Leu Asp Ala Lys Ser Thr Trp Tyr Gly Lys Pro Thr Gly Ala
                20                  25                  30
Gly Pro Lys Asp Asn Gly Gly Ala Cys Gly Tyr Lys Asp Val Asp Lys
                35                  40                  45
Pro Pro Phe Ser Gly Met Thr Gly Cys Gly Asn Thr Pro Ile Phe Lys
50                  55                  60
Ser Gly Arg Gly Cys Gly Ser Cys Phe Glu Ile Lys Cys Thr Lys Pro
65                  70                  75                  80
Glu Ala Cys Ser Gly Glu Pro Val Val Val His Ile Thr Asp Asp Asn
                85                  90                  95
Glu Glu Pro Ile Ala Pro Tyr His Phe Asp Leu Ser Gly His Ala Phe
                100                 105                 110
Gly Ala Met Ala Lys Lys Gly Asp Glu Gln Lys Leu Arg Ser Ala Gly
                115                 120                 125
Glu Leu Glu Leu Gln Phe Arg Arg Val Lys Cys Lys Tyr Pro Glu Gly
                130                 135                 140
Thr Lys Val Thr Phe His Val Glu Lys Gly Ser Asn Pro Asn Tyr Leu
145                 150                 155                 160
Ala Leu Leu Val Lys Tyr Val Asn Gly Asp Gly Asp Val Val Ala Val
                165                 170                 175
Asp Ile Lys Glu Lys Gly Lys Asp Lys Trp Ile Glu Leu Lys Glu Ser
                180                 185                 190
Trp Gly Ala Ile Trp Arg Ile Asp Thr Pro Asp Lys Leu Thr Gly Pro
                195                 200                 205
Phe Thr Val Arg Tyr Thr Thr Glu Gly Gly Thr Lys Thr Glu Ala Glu
                210                 215                 220
Asp Val Ile Pro Glu Gly Trp Lys Ala Asp Thr Ser Tyr Ser Ser Lys
225                 230                 235                 240
```

<210> SEQ ID NO 6
<211> LENGTH: 240
<212> TYPE: PRT
<213> ORGANISM: Unknown
<220> FEATURE:
<223> OTHER INFORMATION: Phl p 1 mutant

<400> SEQUENCE: 6

```
Ile Pro Lys Val Pro Pro Gly Pro Asn Ile Thr Ala Thr Tyr Gly Asp
1               5                   10                  15
Lys Trp Leu Asp Ala Lys Ser Thr Trp Tyr Gly Ala Pro Thr Gly Ala
                20                  25                  30
Gly Pro Ala Asp Asn Gly Gly Ala Cys Gly Tyr Ala Asp Val Asp Ala
                35                  40                  45
Pro Pro Phe Ser Gly Met Thr Gly Cys Gly Asn Thr Pro Ile Phe Lys
50                  55                  60
Ser Gly Arg Gly Cys Gly Ser Cys Phe Glu Ile Lys Cys Thr Lys Pro
65                  70                  75                  80
Glu Ala Cys Ser Gly Glu Pro Val Val Val His Ile Thr Asp Asp Asn
                85                  90                  95
Glu Glu Pro Ile Ala Pro Tyr His Phe Asp Leu Ser Gly His Ala Phe
```

100                 105                 110
Gly Ala Met Ala Lys Lys Gly Asp Glu Gln Lys Leu Arg Ser Ala Gly
                115                 120                 125

Glu Leu Glu Leu Gln Phe Arg Arg Val Lys Cys Lys Tyr Pro Glu Gly
                130                 135                 140

Thr Lys Val Thr Phe His Val Glu Lys Gly Ser Asn Pro Asn Tyr Leu
145                 150                 155                 160

Ala Leu Leu Val Lys Tyr Val Asn Gly Asp Gly Asp Val Val Ala Val
                165                 170                 175

Asp Ile Ala Glu Ala Gly Ala Asp Ala Trp Ile Glu Leu Lys Glu Ser
                180                 185                 190

Trp Gly Ala Ile Trp Arg Ile Asp Thr Pro Asp Lys Leu Thr Gly Pro
                195                 200                 205

Phe Thr Val Arg Tyr Thr Thr Glu Gly Gly Thr Lys Thr Glu Ala Glu
                210                 215                 220

Asp Val Ile Pro Glu Gly Trp Lys Ala Asp Thr Ser Tyr Ser Ser Lys
225                 230                 235                 240

<210> SEQ ID NO 7
<211> LENGTH: 864
<212> TYPE: DNA
<213> ORGANISM: Phleum pratense

<400> SEQUENCE: 7
gccgatctag gttacggccc cgccacccca gctgccccgg tcgccggcta caccccgcc      60 accccgcccg ccccggccgg agcggagcca gcaggtaagg cgacgaccga ggagcagaag    120
ctgatcgaga agatcaacgc cggcttcaag gcggccttgg ccgctgccgc cggcgtcccg    180
ccagcggaca gtacaggac gttcgtcgca accttcggcg cggcctccaa caaggccttc    240
gcggagggcc tctcgggcga gcccaagggc gccgccgaat ccagctccaa ggccgcgctc    300
acctccaagc tcgacgccgc ctacaagctc gcctacaaga cagccgaggg cgcgacgcct    360
gaggccaagt acgacgccta cgtcgccacc ctaagcgagg cgctccgcat catcgccggc    420 acctcgagg tccacgccgt caagcccgcg gccgaggagg tcaaggttat ccctgccggc    480
gagctgcagg tcatcgagaa ggtcgacgcc gccttcaagg tcgctgccac cgccgccaac    540
gccgcgcccg ccaacgacaa gttcaccgtc ttcgaggccg ccttcagcaa cgccatcaag    600
gcgagcacgg cggcgcccta cgagagctac aagttcatcc cgccctgga ggccgccgtc    660 aagcaggcct acgccgccac cgtcgccacc gcgccggagg tcaagtacac cgtcttcgag    720
accgcgctga aaaaggccat caccgccatg tccgaggccc agaaggctgc caagcccgct    780
gccgctgcca ccgccaccgc aacctccgcc gttggcgcgg ccgccggcgc cgccaccgcc    840
gctactggtg gctacaaagt ctga                                           864

<210> SEQ ID NO 8
<211> LENGTH: 864
<212> TYPE: DNA
<213> ORGANISM: Unknown
<220> FEATURE:
<223> OTHER INFORMATION: Phl p 5 mutant

<400> SEQUENCE: 8
gccgatctag gttacggccc cgccacccca gctgccccgg tcgccggcta caccccgcc      60 accccgcccg ccccggccgg agcggagcca gcaggtaagg cgacgaccga ggagcagaag    120
ctgatcgaga agatcaacgc cggcttcaag gcggccttgg ccgctgccgc cggcgtcccg    180

```
ccagcggaca agtacaggac gttcgtcgca accttcggcg cggcctccaa caaggccttc        240
gcggagggcc tctcgggcga gcccaagggc gccgccgaat ccagctccaa ggccgcgctc        300
acctccaagc tcgacgccgc ctacaagctc gcctacaaga cagccgaggg cgcgacgcct        360
gaggccaagt acgacgccta cgtcgccacc ctaagcgagg cgctccgcat catcgccggc        420
accctcgagg tccacgccgt caagcccgcg gccgaggagg tcaaggttat ccttgccggc        480
gagctgcagg tcatcgagaa ggtcgacgcc gccttcaagg tcgctgccac cgccgccaac        540
gccgcgcccg ccaacgacaa gttcaccgtc ttcgaggccg ccttcagcaa cgccatcaag        600
gcgagcacgg gcgcgcccta cgagagctac aagttcatcc ccgccctgga ggccgccgtc        660
aagcaggcct acgccgccac cgtcgccacc gcgccggagg tcaagtacac cgtctttgag        720
accgcgctga aaaaggccat caccgccatg tccgaggccc agaaggctgc caagcccgct        780
gccgctgcca ccgccaccgc aacctccgcc gttggcgcgg ccgccggcgc cgccaccgcc        840
gctactggtg gctacaaagt ctga                                               864

<210> SEQ ID NO 9
<211> LENGTH: 1590
<212> TYPE: DNA
<213> ORGANISM: Unknown
<220> FEATURE:
<223> OTHER INFORMATION: Phl p 1 - Phl p 5 hybrid wt

<400> SEQUENCE: 9
atccccaagg ttcccccggg tccgaacatc acggcgacct acggcgacaa gtggctcgac         60
gcgaagagca catggtacgg caagccgacg ggcgccggtc ccaaggacaa cggcggcgct        120
tgcgggtaca aggacgtgga caagcccccg ttcagcggca tgaccggctg cggcaacacc        180
cctatcttca gtccggccg cggctgcggc tcctgctttg agatcaagtg caccaagccc        240
gaggcctgct ccggcgagcc cgtggtagtc cacatcaccg acgacaacga ggagcccatc        300 gcccctacc acttcgacct ctccggccac gcgttcgggg cgatggccaa gaagggcgat        360
gagcagaagc tgcgcagcgc cggcgagctg gagctccagt tccggcgcgt caagtgcaag        420 taccccggagg gcaccaaggt gaccttccac gtggagaagg ggtccaaccc caactacctg        480
gcgctgcttg tgaagtacgt taacggcgac ggagacgtgg tggcggtgga catcaaggag        540
aagggcaagg acaagtggat cgagctcaag gagtcgtggg gagccatctg gaggatcgac        600
actcccgata gctcacgggg ccccttcacc gtccggtaca ccaccgaggg cggcaccaag        660
accgaagcca aggacgtcat ccctgagggc tggaaggccg acaccagcta ctcgtccaag        720
gaattcgccg atctaggtta cggccccgcc accccagctg cccggtcgc cggctacacc        780 cccgccaccc ccgccgcccc ggccggagcg gagccagcag gtaaggcgac gaccgaggag        840
cagaagctga tcgagaagat caacgccggc ttcaaggcgg ccttggccgc tgccgccggc        900
gtcccgccag cggacaagta caggacgttc gtcgcaacct tcggcgcggc ctccaacaag        960
gccttcgcgg agggcctctc gggcgagccc aagggcgccg ccgaatccag ctccaaggcc       1020
gcgctcacct ccaagctcga cgccgcctac aagctcgcct acaagacagc cgagggcgcg       1080
acgcctgagg ccaagtacga cgcctacgtc gccaccctaa gcgaggcgct ccgcatcatc       1140
gccggcaccc tcgaggtcca cgccgtcaag cccgcggccg aggaggtcaa ggttatccct       1200
gccggcgagc tgcaggtcat cgagaaggtc gacgccgcct tcaaggtcgc tgccaccgcc       1260
gccaacgccg cgcccgccaa cgacaagttc accgtcttcg aggccgcctt cagcaacgcc       1320
```

| | |
|---|---|
| atcaaggcga gcacgggcgg cgcctacgag agctacaagt tcatccccgc cctggaggcc | 1380 |
| gccgtcaagc aggcctacgc cgccaccgtc gccaccgcgc cggaggtcaa gtacaccgtc | 1440 |
| tttgagaccg cgctgaaaaa ggccatcacc gccatgtccg aggcccagaa ggctgccaag | 1500 |
| cccgctgccg ctgccaccgc caccgcaacc tccgccgttg gcgcggccgc cggcgccgcc | 1560 |
| accgccgcta ctggtggcta caaagtctga | 1590 |

<210> SEQ ID NO 10
<211> LENGTH: 1590
<212> TYPE: DNA
<213> ORGANISM: Unknown
<220> FEATURE:
<223> OTHER INFORMATION: Phl p 1 - Phl p 5 hybrid mutant

<400> SEQUENCE: 10

| | |
|---|---|
| atccccaagg ttccccgggg tccgaacatc acggcgacct acggcgacaa gtggctcgac | 60 |
| gcgaagagca catggtacgg cgcgccgacg ggcgccggtc ccgcggacaa cggcggcgct | 120 |
| tgcgggtacg cagacgtgga cgcgcccccg ttcagcggca tgaccggctg cggcaacacc | 180 |
| cctatcttca gtccggccg cggctgcggc tcctgctttg agatcaagtg caccaagccc | 240 |
| gaggcctgct ccggcgagcc cgtggtagtc cacatcaccg acgacaacga ggagcccatc | 300 |
| gcccctacc acttcgacct ctccggccac gcgttcgggg cgatggccaa gaagggcgat | 360 |
| gagcagaagc tgcgcagcgc cggcgagctg gagctccagt ccggcgcgt caagtgcaag | 420 |
| tacccggagg gcaccaaggt gaccttccac gtggagaagg ggtccaaccc caactacctg | 480 |
| gcgctgcttg tgaagtacgt taacggcgac ggagacgtgg tggcggtgga catcgcggag | 540 |
| gcgggcgcgg acgcgtggat cgagctcaag gagtcgtggg gagccatctg gaggatcgac | 600 |
| actcccgata gctcacggg cccttcacc gtccggtaca ccaccgaggg cggcaccaag | 660 |
| accgaagccg aggacgtcat ccctgagggc tggaaggccg acaccagcta ctcgtccaag | 720 |
| gaattcgccg atctaggtta cggccccgcc accccagctg ccccggtcgc cggctacacc | 780 |
| cccgccaccc ccgccgcccc ggccggagcg gagccagcag gtaaggcgac gaccgaggag | 840 |
| cagaagctga tcgagaagat caacgccggc ttcaaggcgg ccttggccgc tgccgccggc | 900 |
| gtcccgccag cggacaagta caggacgttc gtcgcaacct tcggcgcggc ctccaacaag | 960 |
| gccttcgcgg agggcctctc gggcgagccc aagggcgccg ccgaatccag ctccaaggcc | 1020 |
| gcgctcacct ccaagctcga cgccgcctac aagctcgcct acaagacagc cgagggcgcg | 1080 |
| acgcctgagg ccaagtacga cgcctacgtc gccaccctaa gcgaggcgct ccgcatcatc | 1140 |
| gccggcaccc tcgaggtcca cgccgtcaag cccgcggccg aggaggtcaa ggttatcctt | 1200 |
| gccggcgagc tgcaggtcat cgagaaggtc gacgccgcct tcaaggtcgc tgccaccgcc | 1260 |
| gccaacgccg cgcccgccaa cgacaagttc accgtcttcg aggccgcctt cagcaacgcc | 1320 |
| atcaaggcga gcacgggcgg cgcctacgag agctacaagt tcatccccgc cctggaggcc | 1380 |
| gccgtcaagc aggcctacgc cgccaccgtc gccaccgcgc cggaggtcaa gtacaccgtc | 1440 |
| tttgagaccg cgctgaaaaa ggccatcacc gccatgtccg aggcccagaa ggctgccaag | 1500 |
| cccgctgccg ctgccaccgc caccgcaacc tccgccgttg gcgcggccgc cggcgccgcc | 1560 |
| accgccgcta ctggtggcta caaagtctga | 1590 |

<210> SEQ ID NO 11
<211> LENGTH: 723
<212> TYPE: DNA
<213> ORGANISM: Phleum pratense

<400> SEQUENCE: 11

```
atccccaagg ttcccccggg tccgaacatc acggcgacct acggcgacaa gtggctcgac      60
gcgaagagca catggtacgg caagccgacg ggcgccggtc ccaaggacaa cggcggcgct     120
tgcgggtaca aggacgtgga caagcccccg ttcagcggca tgaccggctg cggcaacacc     180
cctatcttca gtccggccg cggctgcggc tcctgctttg agatcaagtg caccaagccc     240
gaggcctgct ccggcgagcc cgtggtagtc cacatcaccg acgacaacga ggagcccatc     300
gcccctacc acttcgacct ctccggccac gcgttcgggg cgatggccaa gaagggcgat     360
gagcagaagc tgcgcagcgc cggcgagctg gagctccagt tccggcgcgt caagtgcaag     420
tacccggagg gcaccaaggt gaccttccac gtggagaagg ggtccaaccc caactacctg     480
gcgctgcttg tgaagtacgt taacggcgac ggagacgtgg tggcggtgga catcaaggag     540
aagggcaagg acaagtggat cgagctcaag gagtcgtggg gagccatctg gaggatcgac     600
actcccgata agctcacggg ccccttcacc gtccggtaca ccaccgaggg cggcaccaag     660
accgaagccg aggacgtcat ccctgagggc tggaaggccg acaccagcta ctcgtccaag     720
tga                                                                   723
```

<210> SEQ ID NO 12
<211> LENGTH: 723
<212> TYPE: DNA
<213> ORGANISM: Unknown
<220> FEATURE:
<223> OTHER INFORMATION: Phl p 1 mutant

<400> SEQUENCE: 12

```
atccccaagg ttcccccggg tccgaacatc acggcgacct acggcgacaa gtggctcgac      60
gcgaagagca catggtacgg cgcgccgacg ggcgccggtc ccgcggacaa cggcggcgct     120
tgcgggtacg cagacgtgga cgcgcccccg ttcagcggca tgaccggctg cggcaacacc     180
cctatcttca gtccggccg cggctgcggc tcctgctttg agatcaagtg caccaagccc     240
gaggcctgct ccggcgagcc cgtggtagtc cacatcaccg acgacaacga ggagcccatc     300
gcccctacc acttcgacct ctccggccac gcgttcgggg cgatggccaa gaagggcgat     360
gagcagaagc tgcgcagcgc cggcgagctg gagctccagt tccggcgcgt caagtgcaag     420
tacccggagg gcaccaaggt gaccttccac gtggagaagg gtccaaccc caactacctg     480
gcgctgcttg tgaagtacgt taacggcgac ggagacgtgg tggcggtgga catcgcggag     540
gcgggcgcgg acgcgtggat cgagctcaag gagtcgtggg gagccatctg gaggatcgac     600
actcccgata agctcacggg ccccttcacc gtccggtaca ccaccgaggg cggcaccaag     660
accgaagccg aggacgtcat ccctgagggc tggaaggccg acaccagcta ctcgtccaag     720
tga                                                                   723
```

<210> SEQ ID NO 13
<211> LENGTH: 25
<212> TYPE: DNA
<213> ORGANISM: Unknown
<220> FEATURE:
<223> OTHER INFORMATION: synthetic oligonucleotide

<400> SEQUENCE: 13

```
caaggttatc cttgccggcg agctg                                            25
```

<210> SEQ ID NO 14

```
<211> LENGTH: 29
<212> TYPE: DNA
<213> ORGANISM: Unknown
<220> FEATURE:
<223> OTHER INFORMATION: synthetic oligonucleotide

<400> SEQUENCE: 14
cgcggtacca tccccaaggt tcccccggg                                       29

<210> SEQ ID NO 15
<211> LENGTH: 26
<212> TYPE: DNA
<213> ORGANISM: Unknown
<220> FEATURE:
<223> OTHER INFORMATION: synthetic oligonucleotide

<400> SEQUENCE: 15
gcgaattcct tggacgagta gctggt                                          26

<210> SEQ ID NO 16
<211> LENGTH: 29
<212> TYPE: DNA
<213> ORGANISM: Unknown
<220> FEATURE:
<223> OTHER INFORMATION: synthetic oligonucleotide

<400> SEQUENCE: 16
cgcgaattcg ccgatctagg ttacggccc                                       29

<210> SEQ ID NO 17
<211> LENGTH: 27
<212> TYPE: DNA
<213> ORGANISM: Unknown
<220> FEATURE:
<223> OTHER INFORMATION: synthetic oligonucleotide

<400> SEQUENCE: 17
gcgggatcct cagactttgt agccacc                                         27

<210> SEQ ID NO 18
<211> LENGTH: 51
<212> TYPE: DNA
<213> ORGANISM: Unknown
<220> FEATURE:
<223> OTHER INFORMATION: synthetic oligonucleotide

<400> SEQUENCE: 18
gcgggtaccc atatgcatca ccatcaccat cacatcccca aggttccccc g              51
```